(12) United States Patent
Foo et al.

(10) Patent No.: US 11,064,749 B2
(45) Date of Patent: Jul. 20, 2021

(54) SYNTHETIC ELASTOMERIC ARTICLE AND METHOD FOR THE PRODUCTION THEREOF

(71) Applicant: SKINPROTECT CORPORATION SDN BHD, Selangor (MY)

(72) Inventors: Khon Pu Foo, Selangor (MY); Chin Keong Lim, Selangor (MY); Cian Ying Tung, Selangor (MY)

(73) Assignee: SKINPROTECT CORPORATION SDN BHD, Selangor (MY)

( * ) Notice: Subject to any disclaimer, the term of this patent is extended or adjusted under 35 U.S.C. 154(b) by 0 days.

(21) Appl. No.: 17/026,586

(22) Filed: Sep. 21, 2020

(65) Prior Publication Data

US 2021/0022422 A1 Jan. 28, 2021

Related U.S. Application Data

(63) Continuation of application No. PCT/AU2020/050054, filed on Jan. 29, 2020.

(30) Foreign Application Priority Data

Jan. 29, 2019 (AU) ................. 2019900254

(51) Int. Cl.
| | | |
|---|---|---|
| *B32B 27/08* | (2006.01) | |
| *B32B 27/18* | (2006.01) | |
| *A61K 45/06* | (2006.01) | |
| *A41D 31/30* | (2019.01) | |
| *A41D 19/00* | (2006.01) | |
| *A61K 35/745* | (2015.01) | |
| *A61K 35/747* | (2015.01) | |
| *A61K 35/00* | (2006.01) | |

(52) U.S. Cl.
CPC ....... *A41D 31/305* (2019.02); *A41D 19/0082* (2013.01); *A61K 35/745* (2013.01); *A61K 35/747* (2013.01); *B32B 27/08* (2013.01); *B32B 27/18* (2013.01); *A61K 45/06* (2013.01); *A61K 2035/115* (2013.01); *B32B 2250/02* (2013.01); *B32B 2250/24* (2013.01); *B32B 2307/54* (2013.01); *B32B 2307/7145* (2013.01); *B32B 2437/02* (2013.01); *B32B 2535/00* (2013.01)

(58) Field of Classification Search
None
See application file for complete search history.

(56) References Cited

U.S. PATENT DOCUMENTS

| | | | |
|---|---|---|---|
| 2004/0142832 A1* | 7/2004 | Runeman | A61Q 19/00 510/130 |
| 2005/0112180 A1* | 5/2005 | Chou | A41D 19/0058 424/443 |
| 2007/0134303 A1 | 6/2007 | Yahiaoui et al. | |
| 2020/0253304 A1* | 8/2020 | Cornelissen | A41D 19/0006 |

FOREIGN PATENT DOCUMENTS

| | | |
|---|---|---|
| WO | 2015/006807 A1 | 1/2015 |
| WO | 2015/006808 A1 | 1/2015 |
| WO | 2017/127861 A1 | 8/2017 |

OTHER PUBLICATIONS

Quezada, M.P., et al., "Acemannan and Fructans from Aloe vera (*Aloe barbadenis* Miller) Plants as Novel Prebiotics", Journal of Agricultural and Food Chemistry, vol. 65, 2017, pp. 10029-10039 (cited in the ISR; in English).
International Search Report and Written Opinion, dated Apr. 9, 2020, issued in counterpart International Application No. PCT/AU2020/050054 (11 pages; in English).

\* cited by examiner

*Primary Examiner* — Sheeba Ahmed
(74) *Attorney, Agent, or Firm* — Westerman, Hattori, Daniels & Adrian, LLP

(57) ABSTRACT

The present application relates to an elastomeric article, such as a glove, comprising: (i) an elastomeric film comprising one or more film layers, and including an external surface and an internal surface, (ii) an antimicrobial agent that is effective against both beneficial and harmful microorganisms on the external surface of the elastomeric film, and (iii) a skin-protective agent selected from a probiotic, a prebiotic, or a combination thereof on the internal surface of the elastomeric film; wherein the inner surface of the film is free of an antimicrobially-effective amount of an antimicrobial agent that is effective against both beneficial and harmful microorganisms. The elastomeric articles may further comprise a barrier film layer that provides separation between the antimicrobial agent and the skin-protective agent. Also described are methods for the manufacture of such articles.

22 Claims, 4 Drawing Sheets

Articles WITHOUT barrier layer

| | Legend |
|---|---|
| (dotted) | Anti-microbial agent |
| (hatched) | Skin Protective agent |
| A | Coagulant layer or/and coating layer |
| A1 | Coagulant layer without anti-microbial agent (does not remain a distinct layer in the final article) |
| B | Elastomeric layer |
| C | Polymer Coating or/and Donning Coating |

Method A/B/C/F(i): A1 | B | C

Method D/F(i): A | B | C

Method D/F(ii): A | B

Method E: A1 | B | B

Method E/F(i): A1 | B | B | C

Method E/F(i)/F(ii): A | B | B | C

Method E/F(i)/F(ii): A | B | B | C

Figure 2

SYNTHETIC ELASTOMERIC ARTICLE AND METHOD FOR THE PRODUCTION THEREOF

CROSS-REFERENCE TO RELATED APPLICATIONS

This application claims the benefit of International Application No. PCT/AU2020/050054 filed on Jan. 29, 2020, which in turn claims priority from Australian Patent Application No. 2019900254 filed on Jan. 29, 2019. The entirety of each of these related applications is hereby incorporated by reference.

FIELD

The present application relates to elastomeric articles and methods for their production. The articles may be of a type intended for contact with the skin of a person. For example, the articles may be in the form of gloves that have antimicrobial properties while also protecting the wearer's skin from exposure to antimicrobial agents.

BACKGROUND

Gloves, such as thin film gloves, are worn in many industries for extended periods of time and provide protection to the wearer from potentially dangerous materials and fluids that the wearer is required to contact in the course of their activities. For example, in the medical industry, health care professionals wear gloves to reduce the risk of being exposed to or transmitting pathogenic microorganisms. The gloves are made from thin films utilising relatively low cost elastomers, yielding a low unit price product, as they are intended to be changed frequently for reasons including hygiene and comfort.

Typical gloves used in such situations are formed from elastomeric films with strong barrier properties. However, while the gloves provide a physical barrier to prevent direct contact and transmission of pathogenic microorganisms to the user's skin, there is a risk that the pathogens are able to pass through the glove to the user's hand. There is also a risk that pathogenic microorganisms that come into contact with the external surface of the glove deposit on the glove, and can then be transmitted to the glove wearer or other people who come into contact with the external glove surface by cross-contamination.

Some gloves containing antimicrobial agents are available. The antimicrobial agents can provide the gloves with antimicrobial properties. The antimicrobial agents are typically present across all glove surfaces. However, the continuous use of such gloves can result in skin problems due to constant exposure of the user's skin to the antimicrobial agent.

The applicant has observed that antimicrobial glove technologies currently on the market do not take into account the potentially damaging effects that repeated exposure to antimicrobial agents can have on the skin.

There is therefore a need for new elastomeric articles, and methods for the production of such articles, that have antimicrobial properties and are also able to provide protection to the skin from repeated exposure to antimicrobial agents contained in the articles, or to at least reduce or minimise the potential damage caused by antimicrobial agents to the skin.

SUMMARY

The applicant has developed new elastomeric articles that contain an antimicrobial agent while also providing protection to the user's skin from exposure to the antimicrobial agent. The applicant has found that by including an antimicrobial agent on an external surface of the article, and a skin-protective agent selected from a probiotic, prebiotic or a combination thereof on an internal surface of the article, it is possible to obtain the benefits of each type of agent without adverse interactions. The applicant was surprised to find that it is possible to obtain elastomeric articles with both antimicrobial and skin protective properties without a prohibitive negative impact on the glove properties, such as elasticity, modulus (fatigue associated with resistance of the glove), softness, film barrier properties, and/or film thickness.

According to the present invention, there is provided an elastomeric article comprising:
  an elastomeric film comprising one or more film layers, and including an external surface and an internal surface,
  an antimicrobial agent on the external surface of the elastomeric film, and
  a skin-protective agent selected from a probiotic, a prebiotic, or a combination thereof on the internal surface of the elastomeric film.

In particular, the present invention provides an elastomeric article comprising:
  an elastomeric film comprising one or more film layers, and including an external surface and an internal surface,
  an antimicrobial agent that is effective against both beneficial and harmful microorganisms on the external surface of the elastomeric film, and
  a skin-protective agent selected from a probiotic, a prebiotic, or a combination thereof on the internal surface of the elastomeric film,
  wherein the inner surface of the film is free of an antimicrobially-effective amount of an antimicrobial agent that is effective against both beneficial and harmful microorganisms.

In addition, there is provided a method for the manufacture of an elastomeric article, the method comprising:
  providing an elastomeric film comprising one or more film layers, the elastomeric film including first and second opposing surfaces;
  introducing an antimicrobial agent onto or into the first opposing surface; and
  introducing a skin-protective agent selected from a probiotic, a prebiotic, or a combination thereof onto or into the second opposing surface.

To ensure that the antimicrobial agent does not appear in any appreciable amount on the inner surface of the film (i.e. to ensure that the inner surface is free of an antimicrobially effective amount of antimicrobial agent that is effective against both beneficial and harmful microorganisms), the step of introducing an antimicrobial agent onto or into the first opposing surface should be performed in a manner so as to avoid the antimicrobial agent from being introduced onto the second opposing surface. Examples of techniques for ensuring this occurs are described in the detailed description.

In preferred aspects, the applicant found that unexpected benefits come from including a layer that is free of both the antimicrobial agent and the skin-protective agent between the external and internal surfaces that contain those agents. This layer functions as a barrier layer, and aids in preserving the efficacy of the skin-protective agent.

Therefore, according to a preferred aspect, there is provided an elastomeric article comprising:

an elastomeric film comprising one or more film layers, and including an external surface and an internal surface, an antimicrobial agent that is effective against both beneficial and harmful microorganisms on the external surface of the elastomeric film, a skin-protective agent selected from a probiotic, a prebiotic, or a combination thereof on the internal surface of the elastomeric film, and a barrier film layer that provides separation between the antimicrobial agent and the skin-protective agent;

wherein the inner surface of the film is free of an antimicrobially-effective amount of an antimicrobial agent that is effective against both beneficial and harmful microorganisms.

According to another preferred aspect, there is provided a method for the manufacture of an elastomeric article, the method comprising:

providing an elastomeric film comprising one or more film layers, the elastomeric film including first and second opposing surfaces;

introducing an antimicrobial agent that is effective against both beneficial and harmful microorganisms onto or into the first opposing surface in a manner so as to avoid the antimicrobial agent from being introduced onto or into the second opposing surface;

introducing a skin-protective agent selected from a probiotic, a prebiotic, or a combination thereof onto or into the second opposing surface; and providing a barrier film layer in the elastomeric film that provides separation between the antimicrobial agent and the skin-protective agent.

In the course of preparing the above films, the applicant has additionally found that very effective articles that are antimicrobial while avoiding excessive irritation to the skin can be prepared without any skin-protective agent on the inner surface. In such instances, care must be taken to ensure that the antimicrobial agent is applied to the external surface of the article, and a barrier layer is also required. According to this particular embodiment, there is accordingly provided an elastomeric article comprising:

an elastomeric film comprising one or more film layers, and including an external surface and an internal surface;

an antimicrobial agent that is effective against both beneficial and harmful microorganisms on the external surface of the elastomeric film; and a barrier film layer between the antimicrobial agent on the external surface of the elastomeric film and the internal surface, to prevent or minimise contact between the antimicrobial agent on the external surface of the elastomeric film and skin that comes into contact with the internal surface of the article, wherein the internal surface of the film is free of an antimicrobially-effective amount of an antimicrobial agent that is effective against both beneficial and harmful microorganisms.

The reference to skin that comes into contact with the internal surface of the article refers to skin that, in use, comes into contact with the inner surface of the article.

According to the present invention, there is provided an elastomeric glove produced by the methods described above.

BRIEF DESCRIPTION OF THE DRAWINGS

The invention will be described in further detail, by way of example only, with reference to the following Figures:

FIG. 2 is a schematic illustration of elastomeric articles without a barrier layer according to embodiments of the invention.

DETAILED DESCRIPTION

Figure 1:
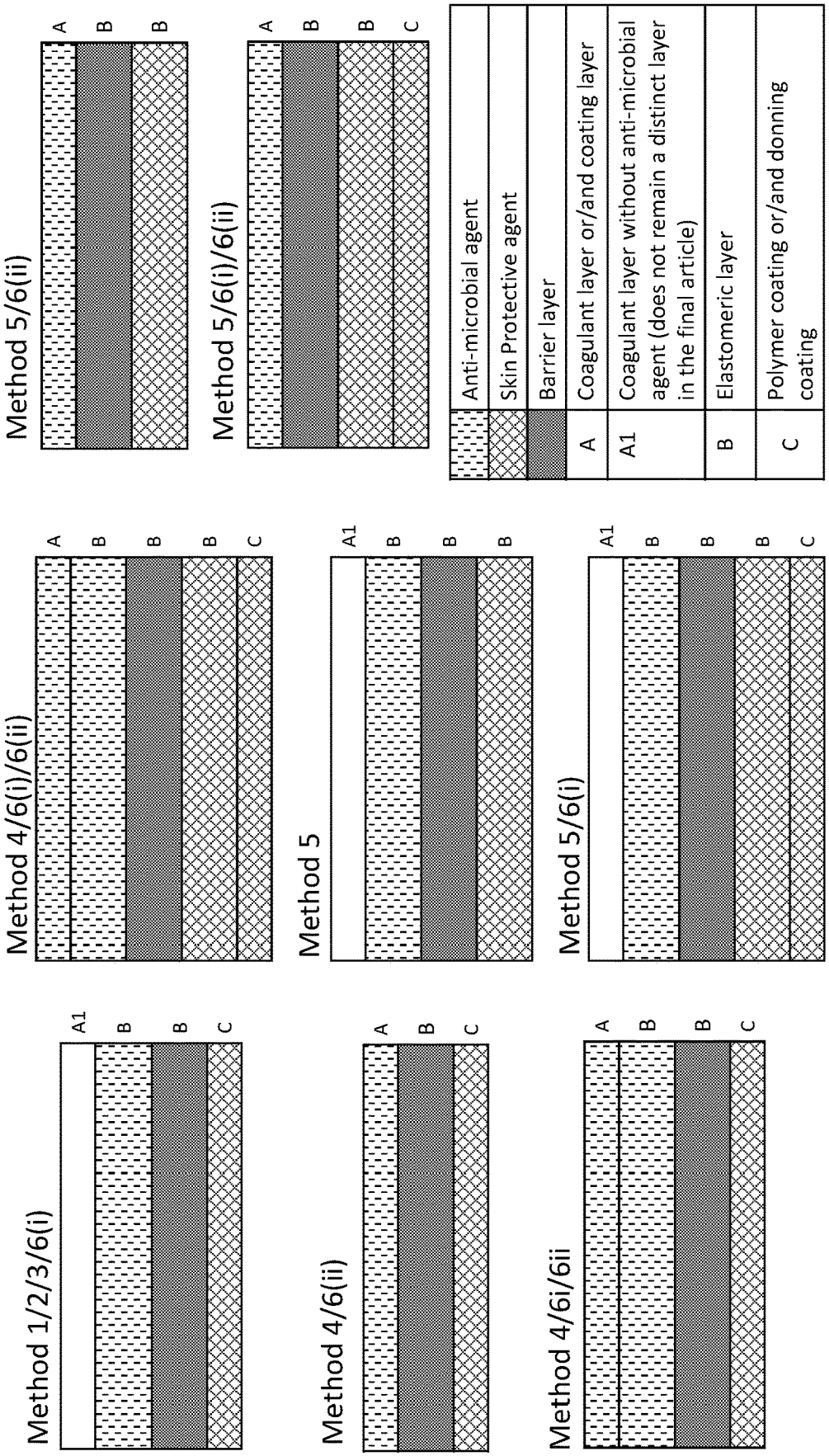
FIG. 1 is a schematic illustration of elastomeric articles containing a barrier layer according to embodiments of the invention.

The elastomeric article and methods of manufacture according to embodiments within the present application are described in further detail in this section.

The following detailed description primarily applies to embodiments of the invention that involve the use of an antimicrobial agent on the external surface of the article, and a skin-protective agent on the inner surface of the article. For embodiments that involve the use of an antimicrobial agent on the external surface (only) and a barrier layer that prevents contact between the antimicrobial agent and the inner surface, the following description should be read as applicable insofar as the features other than the skin-protective agent are described. Thus, where it is described that the skin-protective agent is a key feature, this description is to be understood as only being a relevant comment in relation to those embodiments and claims specifically requiring a skin-protective agent.

Providing Elastomeric Articles with Antimicrobial Properties while Conserving Beneficial Skin Flora Human skin is covered with a diverse community of microorganisms including bacteria and fungi known as skin flora or skin microbiota. Most skin flora reside in the superficial layers of the epidermis and the upper parts of hair follicles.

Skin flora is composed of resident and transient flora. Resident flora are the physiological skin flora. They are generally beneficial microorganisms that have a protective function and do not usually have a pathogenic effect on the skin. Transient flora are episodic microorganisms that can deposit onto the skin but to not adhere to the skin. They are transmissible and can be deposited onto the skin by contact with contaminated substances.

Some transient flora are pathogenic or have the capacity to be pathogenic. Physical barriers, such as gloves and medical dressings, can also be used to prevent direct contact and transmission of pathogenic transient flora to the skin. Some of these products include an antimicrobial agent as an additional means of preventing the transmission of pathogens to the skin, where the antimicrobial agent can come into contact directly or indirectly with the user's skin. However, the antimicrobial agents typically used for these purposes are usually strong enough to kill both pathogenic and beneficial microorganisms on the skin. Therefore, prolonged and frequent exposure of antimicrobial agents to the skin can cause to an imbalance of the community of skin microbiota, particularly the beneficial microorganisms, which may weaken the natural skin barrier over time. This can lead skin problems such as itchiness, dryness, skin sensitivity or allergies, eczema and the like.

There are some glove products available that contain a coating of a skin-moisturising composition on the internal surface (i.e. skin-contacting surface) of the glove. These gloves usually provide a thin layer of a simple composition that provides an apparent skin moisturising effect or apparent skin care properties. Such glove products do not contemplate the concept of providing multiple effects together (antimicrobial and skin microbiota protecting effects).

The applicant has found that providing an elastomeric article having antimicrobial agent on the external surface of the article and a probiotic, a prebiotic, or a combination thereof (grouped by the term "skin-protective agent") on the internal surface of the article provides the article with antimicrobial properties while at the same time reducing the risk of the user having skin problems as a result of repeated exposure to antimicrobial agents. When the article is in use, the probiotics and/or prebiotics on the internal surface of the article are transferred to the user's skin, where they can act to enhance or increase the growth of beneficial skin flora and build a stronger skin barrier against pathogens. Thus, the probiotics and/or prebiotics can counteract the deleterious effects of any antimicrobial agents that may come into contact with the user's skin by conserving beneficial skin flora.

The elastomeric article comprises an elastomeric film having one or more elastomeric film layers. The elastomeric film has two opposing surfaces—one surface is an external surface (that is, an outwardly-facing surface, or non-skin-contacting surface), and the opposite surface is an internal surface (that is, an inwardly-facing surface, or skin-contacting surface). The antimicrobial agent is located towards the external surface of the film, and the skin-protective agent is located towards the internal surface of the film.

The elastomeric article optionally comprises a layer that provides separation between the part of the article that contains or bears the antimicrobial agent, and the part of the article that contains or bears the skin-protective agent. This layer may be referred to as a barrier layer or a separating layer. This layer functions as a barrier layer and does not contain any antimicrobial agents or any probiotics or prebiotics. Accordingly, this layer is referred to as the barrier layer. The barrier layer may be, by way of example, a film layer—that is, an elastomeric film layer, or a coating composition layer (i.e. a coating layer formed from a coating composition). In some embodiments, the barrier layer is specifically a barrier film layer. In relation to articles containing antimicrobial agent and no skin-protective agent, the barrier layer is an essential feature, and this layer provides separation between the antimicrobial agent and the inner surface of the article (e.g. glove).

Elastomeric articles or film products, such as gloves, may be single-layer film products, or multi-layer film products. In this context, the term "layer" refers to the number of elastomeric film layers (i.e. there may be layers of coating compositions or similar in addition to the elastomeric film layer(s)). In the case of a product that contains a single layer of elastomeric film, a barrier layer may be present or it may be absent. If a barrier layer is present, the barrier layer may constitute the single elastomeric film layer. In such embodiments, the antimicrobial agent may be located as a coating on one side of the single film layer, and the skin-protective agent may be located as a coating on the opposite side of the film layer, so that the film layer provides the required barrier between the two agents. (Where there is no skin-protective agent in the article, the antimicrobial agent may be in a coating on one side of the single film layer, without any antimicrobial agent in the inner surface of the film.) The barrier layer in this embodiment is a barrier film layer (i.e. a barrier elastomeric film layer) and can act as a physical barrier to protect the user's skin from pathogens. The barrier film layer can also prevent or reduce the migration of antimicrobial agent on the external surface of the article to the internal surface of the article, where the antimicrobial agent can adversely affect the skin flora and the beneficial effects of the probiotics and/or prebiotics on the internal surface of the article. In an alternative arrangement, the elastomeric article comprising a single layer elastomeric film may comprise (i) an elastomeric film layer containing the antimicrobial agent, followed by (ii) a coating layer on one surface (the internal surface) of the elastomeric film layer, followed by (iii) a coating comprising the skin-protective agent on the coating layer (ii). The coating layer (ii) thus forms a barrier layer between the antimicrobial agent and the skin-protective agent.

In the case of a multi-layered elastomeric article, the article preferably comprises a barrier layer or the article may be free of a barrier layer. When a barrier layer is present, one or more elastomeric film layers of the multilayer film may constitute the barrier layer. In these embodiments, the individual layers form a cohesive film, such that there is no ability to separate the layers. There may also be, to some extent, intermingling between the layers. Regardless, it will be understood (either through the production technique involving the production of film layers of different constitutions, or otherwise) that multiple layers are formed, and that the barrier layer is a layer derived from the film-forming composition that is free of antimicrobial agent and free of skin-protective agent.

It is also possible to produce gloves without a barrier layer. The barrier layer may be omitted if the antimicrobial agent and the skin-protective agents are immobilized within the respective parts of the article (e.g. a layer of elastomeric film or a coating) that contains these agents, without migration of the agents to other parts of the article.

Antimicrobial Agent

The term "antimicrobial agent" refers to a substance that prevents, decreases or inhibits the growth of microorganisms, such as bacteria, viruses, fungi and the like. In the context of the present invention, the term encompasses substances that are capable of preventing, decreasing or inhibiting the growth of pathogens (i.e. microorganisms that can cause disease). The antimicrobial agent may be specifically an antibacterial agent, being an agent that inhibits the growth of bacteria. This can be tested in accordance with the procedure demonstrated in the Examples.

Examples of Suitable Antimicrobial Agents include:
pyrithione compounds such as zinc pyrithione, sodium pyrithione, potassium pyrithione, calcium pyrithione, magnesium pyrithione, and copper pyrithione;
phenolic compounds such as phenoxyethanol, 2-phenylphenol, chlorphenesin, chlorhexylenol, phenoxyisopropanol, triclosan, salicylic acid, and sodium salicylate;
heterocyclic compounds such as piroctone olamine, methylchloroisothiazolinone, methylisothiazolinone, diazolidinyl urea, imidazolidinyl urea, DMDM hydantoin, zinc pyrrolidone carboxylic acid, and sodium pyrrolidone carboxylic acid;
quaternary ammonium salts such as benzethonium chloride, cetylpyridinium chloride, cetrimonium bromide, and myrtrimonium bromide;
biguanide compounds such as chlorhexidine gluconate, and polyaminopropyl biguanide;

parabens such as methyl paraben, ethyl paraben, butyl paraben, propyl paraben, isobutyl paraben, sodium methyl paraben, sodium ethyl paraben, and sodium propyl paraben;

organic acids and their salts including benzoic acid, sodium benzoate, potassium benzoate, calcium benzoate, dehyroacetic acid, sodium dehydroacetate, potassium sorbate, and ethylenediamine tetraacetate;

essential oils such as eucalyptus oil, piper betel oil, menthol, thyme oil, tea tree oil, rosemary oil, peppermint oil, ginger oil, lemongrass oil, and cinnamon bark oil;

antibiotics such as mupirocin, fusidic acid, erythromycin, bacitracin, neomycin, polymyxin b, retapamulin, clindamysin, sulfacetamide sodium, chloramphenicol, benzoyl peroxide, and silver and silver compounds (examples include silver sulfadiazine and silver salts such as silver nitrate, silver chloride and silver oxide);

antiviral agents such as acyclovir, penciclovir, and ganciclovir;

antifungal agents such as selenium disulfide and ketoconazole; and antimicrobial peptides, including in particular antimicrobial peptides of 6-50 amino acid residues with net positive charge.

In some embodiments, the elastomeric article comprises two or more different antimicrobial agents. The different antimicrobial agents may be of the same class (e.g. both may be pyrithiones), or they may be of different classes.

In some embodiments, the antimicrobial agent comprises at least one pyrithione compound. In one embodiment, the antimicrobial agent comprises zinc pyrithione and sodium pyrithione.

In some embodiments, the antimicrobial agent comprises at least one phenolic compound and at least one heterocyclic compound. In one embodiment, the antimicrobial agent comprises 2-phenylphenol and piroctone olamine.

In some embodiments, the antimicrobial agent comprises at least one phenolic compound, at least one heterocyclic compound and at least one essential oil. In one embodiment, the antimicrobial agent comprises phenoxyethanol, zinc pyrrolidone carboxylic acid, and piper betel oil.

Of the antimicrobial agents described, the following are most preferred:

Pyrithione compounds: these compounds are most suited to addition into the latex composition to form a latex layer containing the pyrithione antimicrobial agent. Pyrithione is available in dispersion form and is not soluble in water. Consequently, it is able to be incorporated into the latex, and has been found to remain within the latex film layer without being readily leached out during leaching stages of production.

Phenolic compounds: these compounds are most suitably incorporated into the article through addition into the coagulant, or application through a coating composition, or through both techniques. Phenolic compounds tend to be oily liquids, with poor water solubility, however they have high temperature stability and good efficacy against a wide range of bacteria. It has been found that they best added through a coagulant or a coating composition to achieve the best overall film properties. Alternatively, phenolic compounds may be emulsified prior to addition into a water-based coagulant composition, water-based coating solution or water-based latex, to address the oiliness of the compound. Examples of suitable emulsifiers for this purpose include ceteareth-20, cetearyl alcohol, PEG-40, castor oil, glyceryl stearate, sodium lauryl sulfate, sodium cetearyl sulfate, cetyl palmitate and so forth. Alternatively, the oily phenolic compounds can be mixed with a solubiliser such as polysorbate 20, 60, 80 before being added into a water-based coating solution. This method can be used with any oily antimicrobial agent, and not just the phenolic compounds.

Of the antimicrobial agents, the following are also useful:

Heterocyclic compounds: those heterocyclic compounds that are effective and stable within the pH range of the latex composition are most preferred. The latex composition typically has a pH above 7.0 (usually above 8.0 or higher).

Quaternary ammonium salts: When used, it is preferred that these salts are introduced through addition into the coagulant and/or through addition into a coating composition.

Biguanides: These compounds are suitable for use in this application, but in some embodiments the antimicrobial agent selected is a non-biguanide antimicrobial agent.

Parabens: These compounds can be used but are less preferred due to potential concerns with the presence of parabens in personal care products.

Organic acids and their salts, when used, should be introduced via the coagulant or coating composition. Essential oils may be used, but are not particularly preferred, as they tend to have a lower antimicrobial efficacy compared to other agents described herein. Nevertheless, essential oils are useful in combination with additional classes of antimicrobial agents. An agent selected from the class of antibiotics and antiviral agents may be used in conjunction with another antimicrobial agent, to provide a broader spectrum of efficacy against viruses and/or antibiotic-resistant bacteria. Any newly developed antimicrobial agents may additionally or alternatively be used, provided they can be incorporated into the latex composition, coagulant and/or coating in a manner such that they do not impair the film properties and do not transmit across the barrier film layer in the final product.

The antimicrobial agents contemplated for use as the antimicrobial agent used in the present application are those that are effective against both beneficial and harmful microorganisms. On a strained interpretation, it may be considered by some persons in the art that some probiotics have "antimicrobial" properties, in that they may provide an environment that does not encourage the growth of harmful microorganisms. Accordingly, to avoid ambiguity, it is noted that the term "antimicrobial" refers to antimicrobial agents that are effective against both beneficial and harmful microorganisms. The efficacy against beneficial microorganisms is, at least, one distinction between antimicrobials and probiotics.

Particular claims of the present application require that the inner surface of the film is free of an antimicrobially-effective amount of an antimicrobial agent (i.e. an antimicrobial that is effective against both beneficial and harmful microorganisms). Those skilled in the art would be able to conduct tests to determine whether there is an effective amount of such an antimicrobial agent on a particular surface, and to determine to their satisfaction that there is no (or insufficient) antimicrobial on that surface to be effective against beneficial and harmful microorganisms. The Examples provided herein provide guidance on techniques to be used. The test microorganism to be used to test for efficacy against beneficial microorganisms is *Lactobacillus casei*. The test microorganism to be used to test for efficacy against harmful microorganisms is *Staphylococcus aureus*.

The test results should be indicative of the fact that no significant amount of antimicrobial agent has been applied to the inner film surface of the article.

If a particular test is required to provide a uniform standard for determining compliance with the requirement that "the inner surface of the film is free of an antimicrobially-effective amount of an antimicrobial agent", the following test may be applied:

Test Procedure
1. Prepare de Man, Rogosa and Sharpe (MRS) agar plate was prepared using MRS agar powder.
2. Spread a 100 µL of *Staphylococcus aureus* dissolved in peptone water on the MRS agar.
3. Place a 1.6 cm diameter round shaped specimen of the glove sample on the plate, with the surface being tested placed downwards on the plate.
4. Incubate the plate at 36° C. for 48 hours.
5. Measure the size of zone inhibition following incubation, from the edge of the glove specimen to the edge of the zone inhibition, based on an average of three different locations to allow for variations around the sample.
6. Repeat steps 1-5 using *Lactobacillus casei* in place of *Staphylococcus aureus*.
7. A zone size of 4 mm or less for each tested microorganism indicates that the relevant surface of the film is free of an antimicrobially-effective amount of an antimicrobial agent.

The value of 4 mm accounts for the fact that the opposite surface contains antimicrobial agent, and as shown in Example 8, there is some degree of potential transmission of antimicrobial agent through the film. This is impeded if certain preferred features (such as a barrier layer with lamellar filler) are present in the article.

In some embodiments, it may be described that the inner surface is free of any antimicrobial agent (noting that this term excludes probiotics and/or prebiotics).

If one is aware of the exact procedure used to produce the article, and the production technique involves no application of the antimicrobial onto or into to the inner surface of an article, and it is clear from the manner of incorporation into or onto the outer surface that no antimicrobial should have found its way onto the inner surface, then these facts can be relied on in place of the above test procedure. This may assist manufacturers to avoid the need to complete the test where their manufacturing techniques clearly avoid application of antimicrobial to the inner surface of the article. However, if the method of manufacture presents a question as to whether an effective amount of an antimicrobial might be found on the inner surface of the article, then the above test procedure takes precedence.

Incorporation of Antimicrobial Agent into the Elastomeric Article

The antimicrobial agent may be included on the external surface (i.e. non-skin-contacting surface) of the elastomeric article in any way that provides the elastomeric article with antimicrobial properties on the external surface.

The three main ways the antimicrobial agent can be included on the external surface of the elastomeric article is through:
(i) incorporating the antimicrobial agent into an elastomeric film-forming composition used to produce one of the film layers of the elastomeric film (being the film layer that will become the outermost elastomeric film layer of the film);
(ii) incorporating the antimicrobial agent into the coagulant composition used when making the elastomeric article; and/or
(iii) applying a coating composition comprising the antimicrobial agent to the external surface of the elastomeric article.

In the case of technique (ii), this results in the antimicrobial agent becoming incorporated into the first-formed elastomeric film layer of the article.

The antimicrobial agent may be included through any one of these techniques (i) to (iii), or through a combination of two techniques (e.g. (i) and (ii), (i) and (iii), or (ii) and (iii), or all three.

Preferably, the antimicrobial agent is incorporated into a film layer on the external surface of the elastomeric article, which may be by inclusion of the antimicrobial agent in a coagulant and/or in an elastomeric film-forming composition used to prepare a film layer of the elastomeric article.

In the following we describe incorporation of the antimicrobial agent into a film-forming composition first, then incorporation of the antimicrobial agent into the coagulant, then the coating technique for the application of the antimicrobial agent onto the film surface. In a later section, additional details of the methods used to incorporate the antimicrobial agent are described, including information on the concentrations of components that may be used in the various formulations.

Antimicrobial Agent within a Layer of the Elastomeric Film

One technique for incorporating the antimicrobial agent into the elastomeric film is by way of including the antimicrobial agent in the latex composition (elastomeric film-forming composition) that is used to form a layer of the elastomeric article. As one example, the antimicrobial agent is mixed into an elastomeric film-forming composition, and a former (e.g. a glove-shaped former) is dipped into the elastomeric film-forming composition to form a shaped elastomeric film layer containing the antimicrobial agent.

In embodiments where the antimicrobial agent is incorporated into the elastomeric film layer, the elastomeric article may comprise a single-layer film. In these embodiments, where the article includes a barrier layer, the article comprises a coating on the internal surface (i.e. skin-contacting surface) of the article containing the skin-protective agent, and a barrier coating layer between the single layer film and the coating containing the skin-protective agent. In other embodiments, the elastomeric article may comprise a multilayer film having at least 2 layers. In these embodiments, the multilayer film comprises an external film layer that forms the outwardly-facing surface of the article, and an internal film layer which is in contact with the user's skin when the article is in use. There may be additional film layers between the external film layer and the internal film layer. The multilayer film optionally comprises a barrier film layer between the external layer incorporating the antimicrobial agent, and the skin-protective on the internal surface of the article. The internal film layer may be the barrier film layer, or there may be another barrier film layer between the external and internal film layers.

Depending on the manner of inclusion of the antimicrobial agent into the elastomeric film-forming composition, the antimicrobial agent may migrate to the external surface of the elastomeric article upon storage, thus providing antimicrobial properties to the external surface of the elastomeric article. The antimicrobial agent may alternatively remain throughout the layer of elastomeric film (matrix), but at a concentration or in an amount such that the external surface of the elastomeric article has antimicrobial properties.

When included in a film layer, the amount of antimicrobial agent in the final elastomeric film product may be between 0.001% and 15% by weight, based on the weight of the elastomeric film. This amount is based on the broad phr content of the antimicrobial agent within the elastomeric film-forming composition for producing an external film layer, and allows for the addition of one or more barrier layers (when present) in the case of multi-layered films, and some potential leaching of the antimicrobial agent from the film during the production of the article.

Antimicrobial Agent Introduction through Incorporation into the Coagulant

When making dipped elastomeric film products, such as gloves, the process typically involves dipping a former (i.e. a mould) into a coagulant, followed by dipping into an elastomeric film-forming composition. A coagulant layer is left on the former after the coagulant dipping step. The coagulant layer on the former attracts a layer of film-forming composition onto the surface of the former, at a desired thickness that is dependent on the coagulant composition and concentration. There is interpenetration of the layer of coagulant into the layer of elastomeric film that is attracted to the former surface when the film dipping step is performed.

It is possible to introduce the antimicrobial agent into the elastomeric film by including the antimicrobial agent in the coagulant used in the production of the elastomeric film. In the final product, the distribution of antimicrobial agent will be consistent with the antimicrobial agent being present in a coagulant composition used in the preparation of the elastomeric article. The concentration of antimicrobial agent may be greater at the former-contacting surface, which typically becomes the external surface of the article after the elastomeric film is stripped from the former (i.e. stripping inverts the article, resulting in the coagulant-side of the film becoming the outward-facing surface of the article). The amount of antimicrobial agent in the coagulant needs to be sufficient to provide the external surface of the elastomeric article with antimicrobial properties.

The antimicrobial agent in the form of a water-soluble liquid, water-soluble solid, emulsion or dispersion can be mixed directly into the coagulant composition. The coagulant composition may contain the usual coagulant composition components (as described in further detail below), with the addition of 0.001% to 50%, preferably 0.01% to 10% by weight of the antimicrobial agent.

In embodiments where the antimicrobial agent is introduced into the elastomeric film by incorporation into the coagulant, the elastomeric article may comprise a single-layer film. In these embodiments, where the article includes a barrier layer, the article comprises a coating on the internal surface (i.e. skin-contacting surface) of the article containing the skin-protective agent, and a barrier coating layer between the single layer film and the coating containing the skin-protective agent. In other embodiments, the elastomeric article comprises a multilayer film having at least 2 layers. In these embodiments, the multilayer film comprises an external film layer that forms the outwardly-facing surface of the article, and an internal film layer which is in contact with the user's skin when the article is in use.

There may be additional film layers between the external film layer and the internal film layer. The multilayer film optionally comprises a barrier film layer between the external layer incorporating the antimicrobial agent, and the skin-protective agent on the internal surface of the article. The internal film layer may be the barrier film layer, or there may be another barrier film layer between the external and internal film layers.

Antimicrobial Agent provided as a Coating on the Elastomeric Film

In another example, the antimicrobial agent can be incorporated into the elastomeric article by the application of the antimicrobial agent or a coating composition containing the antimicrobial agent onto an elastomeric film product. Thus, the elastomeric article may include a coating layer comprising the antimicrobial agent.

In embodiments where the antimicrobial agent is in a coating layer, the coating layer comprising the antimicrobial agent is present on the external surface of the article. The coating layer comprises the antimicrobial agent in an amount sufficient to provide the elastomeric article with antimicrobial properties. It is noted that the antimicrobial agent is on the external surface of the article, only, and not on the internal surface of the article. Thus, the application needs to be such as to control the application onto that single surface. Otherwise, there may be an adverse interaction and/or reduction in the efficacy of the antimicrobial agent or the skin-protective agent.

A manufacturer of products in accordance with the present application can purchase in elastomeric articles and apply the coating composition comprising the antimicrobial agent to the articles, or the manufacturer can produce the elastomeric articles and then apply the coating composition. Methods for the manufacture of elastomeric articles which may be subjected to a coating step are described herein. The elastomeric articles subjected to the coating step may themselves contain an antimicrobial agent (and/or a probiotic, a prebiotic, or a combination thereof) in the elastomeric film itself, or they may be free of such agents.

Where reference is made to "providing" an elastomeric film, this expression is used to encompass the step of obtaining such films from a manufacturer of such films (e.g. a glove supplier), or the manufacturing steps for the production of the elastomeric film. Where reference is made to "providing" a barrier layer in the elastomeric film that provides separation between an antimicrobial agent and the skin-protective agent, this term encompasses simply ensuring that the antimicrobial agent and skin-protective agent(s) are applied to opposite surfaces of a film obtained from a film supplier (e.g. a glove supplier/manufacturer), or the step of manufacturing the glove so as to include or incorporate a barrier layer. Thus, where one is manufacturing the entire glove, the method may comprise:

producing an elastomeric film comprising one or more film layers, the elastomeric film including first and second opposing surfaces;

introducing an antimicrobial agent onto or into the first opposing surface;

introducing a skin-protective agent selected from a probiotic, a prebiotic, or a combination thereof onto or into the second opposing surface; and incorporating a barrier layer in the elastomeric film that provides separation between the antimicrobial agent and the skin-protective agent.

The barrier layer may be layer of elastomeric film that does not contain any antimicrobial agents or any skin-protective agents. Alternatively, the barrier layer may be a coating layer between a film layer containing an antimicrobial agent and a coating layer containing a skin-protective agent, or between a film layer containing a skin-protective agent and a coating containing an antimicrobial agent.

The barrier layer incorporation step can be omitted. This step can be omitted if the antimicrobial agent and the skin-protective agents are immobilized within the respective parts of the article that contains these agents, without migration of the agents to other parts of the article.

The total weight of the (dried) coating containing an antimicrobial agent (i.e. following removal of solvent such as water) may be between 0.001 and 30% by weight of the elastomeric article. The weight percentage of the article taken up by the coating layer containing the antimicrobial agent in the final product (i.e. a dried weight) may be a minimum of 0.001%, 0.01%, 0.1%, 1% or 5% by weight (based on the total article weight). The weight percentage of the article taken up by the coating containing the antimicrobial agent may be less than 30%, 25%, 20%, 15%, 10% or 5% by weight of the total article weight. Any minimum and maximum can be combined to form a range, provided that the maximum is greater than the minimum, such as a range of between 0.1% and 25%.

In some embodiments, the antimicrobial agent constitutes about 0.001% to 75% by weight of the total weight of the article. The weight percentage of the article taken up by the antimicrobial agent in the final product (i.e. a dried weight) may be a minimum of 0.001%, 0.01%, 0.1%, 1% or 5% by weight (based on the total article weight). The weight percentage of the article taken up by the coating containing the antimicrobial agent may be less than 30%, 25%, 20%, 15%, 10% or 5% by weight of the total article weight. Any minimum and maximum can be combined to form a range, provided that the maximum is greater than the minimum, such as a range of between 0.1% to 5% by weight of the total weight of the article.

In some embodiments, the total amount of antimicrobial agent in the coating layer is at least 5% by weight of the coating layer. For example, the total amount of antimicrobial agent in the coating layer may be a minimum of about 10%, 20%, 30%, 40% or 50% of the coating layer, and up to 75%.

In the example of a glove, weighing approximately 4 g (prior to coating), the coating composition may be applied in a typical amount of at least 0.001 mg of dried antimicrobial agent, such as at least 0.005 mg, at least 0.01 mg, at least 0.05 mg, at least 0.1 mg, at least 0.5 mg, or at least 1 mg of dried antimicrobial agent. In preferred embodiments, the glove coating composition may be applied in an amount of about 4 mg to 1000 mg of dried antimicrobial agent, equivalent to 0.1% to 25% by weight of the total glove weight. Expressed another way, the volume of coating composition containing the antimicrobial agent picked up by a glove is about 0.1 mL or more, preferably about 0.5 mL to about 5 mL per glove. These amounts also serve as a useful guide for a range of other articles, although the amounts may vary depending on the size of the article.

Skin-Protective Agents

The term "skin-protective agent" is used to refer to any agent classified as a prebiotic or a probiotic. At least one skin-protective agent within these classes is required on one surface of the article—generally the internal surface that comes into contact with the wearer of the article. The reference to such an agent being on the surface extends to encompass the presence of such an agent within a film layer that defines the surface of the article (e.g. the surface on the inside of the article) in such a manner as to come into contact with the skin in use or when worn. There may be additional very thin coating layers (e.g. ultra thin polymer coating film) on the article on top of the skin-protective agent (especially when that agent is present in an elastomeric film layer), provided that the skin-protective agent is able to contact and/or transfer to the skin of the wearer. In some specific embodiments, the skin protective agent may be in the final coating layer on the article, on the surface facing inwardly to the skin of the wearer (when worn).

Probiotics and/or prebiotics have the ability to improve, supplement or increase the growth of beneficial microorganisms that reside on the skin (i.e. the residential skin flora), but not one or more pathogens. Examples of beneficial skin microbiota include *Staphylococcus capitis*, *Corynebacterium xerosis*, *Micrococcus kristinae*, *Micrococcus lylae*, *Micrococcus sedentarius*, *Lactobacillus pentosus*, *Lactobacillus gasseri*, *Lactobacillus salivarius*, and *Lactobacillus acidophillus*. Examples of undesirable or pathogenic skin microbiota include *Candida albicans*, *Staphylococcus aureus*, *Staphylococcus epidermis*, *Corynebacterium minutissimum*, *Propionibacterium acnes*, *Propionibacterium granulosum*, *Salmonella typhimurium*, *Escherichia coli*, *Malassezia furfur*, and *Pseudomonas aeruginosa*. Publications demonstrating the beneficial effect of probiotics and/or prebiotics on the skin include: 1. Ji Hye Jeong, Chang Y. Lee & Dae Kyun Chung (2016) Probiotic Lactic Acid Bacteria and Skin Health, *Critical Reviews in Food Science and Nutrition*, 56:14, 2331-2337; 2. Al-Sheraji, S. H., Ismail, A., Manap, M. Y., Mustafa, S., Yusof, R. M., Hassan, F. A. (2013) Prebiotics as functional foods: A review, *Journal of Functional Foods*, 5, 1542-1553; 3. Al-Ghazzewi, F. H., and Tester R. F. (2014) Impact of prebiotics and probiotics on skin health, *Beneficial Microbes*, 5(2): 99-107; 4. Berardesca, E., Abril, E., Serio, M. and Cameli, N. (2009) Effects of topical gluco-oligosaccharide and collagen tripeptide F in the treatment of sensitive atopic skin, *international Journal of Cosmetic Science*, 31, 271-277.

Probiotics

The term "probiotic" encompasses beneficial microorganisms which, when administrated in adequate amounts, strengthen or improve the properties of the indigenous skin flora, or enhance the growth of a beneficial microorganism within the skin flora. The term extends to include live cultures, freeze-dried cultures, extracts or lysates of such microorganisms. The extracts are multi-component extracts, such as aqueous or organic extracts of the microorganisms or lysates thereof. Probiotics can contribute towards the skin defence barrier by reducing the capacity of pathogens to colonise on the skin. Several mechanisms for probiotic activity have been postulated, including competition with pathogens for nutrients, immunomodulation, and production of antimicrobial metabolites. Microorganisms that are beneficial to the skin are the subject of many publications, and it is open to the skilled person to determine with reference to such publications whether a particular microorganism is one that is beneficial to skin. Suitable probiotics that are beneficial microorganisms in this context are described below.

Examples of suitable probiotics include lactic acid producing probiotics such as *Lactobacillus* and *Lactococcus*, and *Bifidobacterium*. *Lactobacillus* subspecies include *Lactobacillus brevis*, *Lactobacillus acidophilus*, *Lactobacillus casei*, *Lactobacillus lactis*, *Lactobacillus plantarum*, *Lactobacillus pentosus*, *Lactobacillus gasseri*, *Lactobacillus salivarius*, *Lactobacillus rhamnosus*, *Lactobacillus reuteri*, *Lactobacillus delbreuckii*, and *Lactobacillus paracasei*. *Lactococcus* subspecies include *Lactococcus lactis*. *Bifidobacterium* species include *Bifidobacterium longum*, *Bifidobacterium breve*, and *Bifidobacterium infantis*. Other species of *Bifidobacterium*, *Lactococcus* and *Lactobacillus*, and also those of the genera *Bacillus*, *Enterococcus*, *Streptococcus* and *Saccharomyces* classified as probiotics or shown to have probiotic effect may also be considered. These probiotics may be in the form of live cultures, freeze-dried cultures, or extracts or lysates thereof.

In some embodiments, the probiotic is selected from the following (including extracts/lysates thereof):
- a *Lactobacillus* selected from *Lactobacillus brevis*, *Lactobacillus acidophilus*, *Lactobacillus casei*, *Lactobacillus lactis*, *Lactobacillus plantarum*, *Lactobacillus pentosus*, *Lactobacillus gasseri*, *Lactobacillus salivarius*, *Lactobacillus rhamnosus*, *Lactobacillus reuteri*, *Lactobacillus delbreuckii*, and *Lactobacillus paracasei*;
- a *Lactococcus* selected from *Lactococcus lactis*; or
- a *Bifidobacterium* selected from *Bifidobacterium longum*, *Bifidobacterium breve*, and *Bifidobacterium infantis*.

In some embodiments, the elastomeric article comprises two or more different probiotics. The different probiotics may be of the same species (e.g. both may be *Lactobacillus* subspecies), or they may be of different species.

In some embodiments, the probiotic comprises *Lactobacillus*. In some embodiments, the probiotic comprises *Bifidobacterium*.

In some embodiments, the probiotic is a thermophile, such as a hyperthermophile. A thermophile is a microorganism that have an optimum growth temperature of 50° C. or higher. Hyperthermophiles have an optimum growth temperature of above 75° C. An example of a thermophile is *Lactobacillus delbreuckii*. Other examples include thermophiles isolated from hot spring water, such as those of the *Bacillus* species, such as *Bacillus subtilis*, *Geobacillus pallidus* and *Anoxybacillus flavithermus*. Thermophiles used in yogurt/cheese production may also suit, such as *Streptococcus thermophilus* and *Lactobacillus delbrueckii* subsp. *Bulgaricus*.

The probiotic may be present in the form of a live culture, an extract, a ferment lysate, or may be freeze-dried. In preferred embodiments, the prebiotic is in the form of a ferment lysate or extract, such as a ferment lysate or extract of *Lactobacillus*. The applicant has discovered that probiotics in the form of a ferment lysate or extract are compatible with the manufacturing methods used to prepare the elastomeric articles described herein and can be preserved at room temperature.

Prebiotics

The term "prebiotic" refers to a substance that is a nutrient source for beneficial microorganisms, and in particular, for the beneficial residential skin flora and/or any probiotics present. The term encompasses substances that enhance the viability and/or activity of the beneficial microorganisms in the residential skin flora. For example, prebiotics in the form of short-chain carbohydrates (up to 10 sugar/carbohydrate units) can be fermented by beneficial residential skin flora and/or probiotics to produce short chain fatty acids such as lactic acid, acetic acid, propionic acid and butyric acid, which can be used by the beneficial microbes as an energy source to enhance their growth and proliferation. Prebiotics are capable of being metabolized by beneficial microorganisms, but not pathogens, and therefore selectively enhance the viability and/or activity of the beneficial microorganisms. Expressed another way, prebiotics are substances that are selective substrates for one or a limited number of beneficial microorganisms but are not preferential substrates for pathogens.

Examples of suitable prebiotics include saccharides such as alpha-glucan, beta-glucan, sodium carboxymethyl beta-glucan, magnesium carboxymethyl beta-glucan, glucomannan oligosaccharides, inulin, fructooligosaccharides, galactooligosaccharides, xylooligosaccharides, arabinoxylan oligosaccharides, mannooligosaccharides, pectin, lignin, psyllium, chitin, chitosan, and biotin. Other examples of suitable prebiotics include phytosphingosine and its salts/derivatives such as phytosphingosine hydrochloride, lactic acid, glycomacropeptide, and amino acids and peptides. Suitable prebiotics can also include prebiotics derived from a plant source such as chicory root (e.g. fructooligosaccharides, inulin), Jerusalem artichoke (e.g. fructooligosaccharides), yacon root, beetroot (e.g. fructooligosaccharides), burdock root, konjac root (e.g. konjac glucomannan), jicama root, dandelion greens, barley (e.g. fructooligosaccharides), wheat bran (e.g. xylooligosaccharides and arabinoxylooligosaccharides), apple, oats, yeast and brown rice.

In some embodiments, the prebiotic selected from the following:
- a saccharide selected from alpha-glucan, beta-glucan, sodium carboxymethyl beta-glucan, magnesium carboxymethyl beta-glucan, glucomannan oligosaccharides, inulin, fructooligosaccharides, galactooligosaccharides, xylooligosaccharides, arabinoxylan oligosaccharides, mannooligosaccharides, pectin, lignin, psyllium, chitin, chitosan, and biotin;
- phytosphingosine and derivatives or salts thereof, such as phytosphingosine hydrochloride;
- lactic acid;
- glycomacropeptide; or
- amino acids and peptides.

In some embodiments, the elastomeric article comprises two or more different prebiotics. The different prebiotics may be of the same class (e.g. both may be saccharides), or they may be of different classes.

In some embodiments, the prebiotic comprises a saccharide selected from the group consisting of alpha-glucan, beta-glucan, fructooligosaccharides, inulin, and combinations of one or more thereof. In some embodiments, the prebiotic comprises plurality of saccharides, such as alpha-glucan, beta-glucan, fructooligosaccharides and inulin.

The prebiotic may in some embodiments be an "isolated prebiotic". This term is used to refer to isolated or more purified forms of prebiotics, to the exclusion of less purified plant extracts that contain low levels of compounds that may be within the classes of prebiotics described above. Thus, as one notable example, aloe vera (the liquid pressing from the aloe vera plant) falls outside the scope of the term "isolated prebiotic". An "isolated prebiotic" is a substance containing the prebiotic (or combination of prebiotics) at a concentration of at least 20%, preferably at least 30%, 40% or at least 50%, excluding water, stabilisers and emulsifiers. Such isolated prebiotic compositions may be supplied as an aqueous solution or suspension of the prebiotic. As one example, CM-glucan is an example of a commercially available beta-glucan prebiotic composition. The composition comprises 2% by weight beta-glucan, about 20% by weight of stabilizers and emulsifiers (total), and the balance water. Excluding the water and stabiliser/emulsifier content, the composition is predominantly prebiotic. Isolated prebiotics are less likely to give rise to allergies or skin sensitivity problems, compared to complex plant extracts.

The elastomeric article may comprise at least one probiotic, at least one prebiotic, or at least one probiotic in combination with at least one prebiotic.

The skin-protective agent is preferably other than aloe vera. The skin-protective agent is preferably an agent other than aloe vera or a substance derived from aloe vera.

Combinations

In some embodiments, the elastomeric article comprises at least one probiotic and at least one prebiotic. In such embodiments, the prebiotic may be suitably selected as a nutrient source for the selected probiotic. In these embodiments, the probiotics and prebiotics can complement each other to improve properties of the beneficial skin flora.

In some embodiments, the probiotic is a *Lactobacillus* and the prebiotic is a saccharide. In one embodiment, the probiotic is a *Lactobacillus* and the prebiotic is a saccharide selected from the group consisting of alpha-glucan, beta-glucan, fructooligosaccharides, inulin and combinations thereof.

Incorporation of Skin-Protective Agent into the Elastomeric Article

A skin-protective agent is included on the internal (skin-contacting) surface of the elastomeric article. When the article is on a former (during production of the article), this surface typically forms the outermost surface of the article on the former, which is then inverted on removal from the former to become the inner surface of the article.

The two main ways the skin-protective agent can be included on the internal surface of the elastomeric article is through:
  (i) applying a coating composition comprising the skin-protective agent to the internal surface of the elastomeric article (which may be inverted at the time of application, so that the coating is applied onto the outer surface prior to inversion to form the inner surface of the article); and/or
  (ii) incorporating the skin-protective agent into an elastomeric film-forming composition.

The skin-protective agent may be included through either technique (i) or (ii), or both techniques.

In embodiments where the elastomeric article comprises more than one skin-protective agent (of the same or different classes), these may each be included into the article through the same or different techniques. In one example, one or more probiotics may be incorporated into a film layer on the internal surface of the article and one or more prebiotics may be included in a coating layer on the internal surface of the article, or vice versa. One, some, or all of the probiotic(s) in the internal film layer may be the same as those in the coating layer, or they may be different. In some embodiments, the skin-protective agents (where there are more than one) are incorporated through one technique.

Preferably, the skin-protective agent is applied as a coating on the internal surface of the elastomeric article. The coating composition comprising the skin-protective agent may be a polymer coating composition. Polymer coating compositions have been proposed previously for providing elastomeric articles such as gloves with "slip" properties to aid donning, but such polymer coatings have not been known to include any agents within the range of skin-protective agents as described herein.

In embodiments where the skin-protective agent is incorporated into one elastomeric film layer of the elastomeric article, the elastomeric article may be a single-layer film or a multi-layer film. In the case of a single layer film, if the article includes a barrier layer, the article may comprise a coating containing the antimicrobial agent on the external surface (i.e. the outwardly-facing surface) of the article, and a barrier coating layer between the single layer film and the coating containing the antimicrobial agent. In the case of a multi-layer film, according to one option, one layer forms a barrier layer of the film, and another film layer comprises the skin-protective agent, with the anti-microbial agent located on the opposite side of the multilayered film as compared to the skin-protective agent-containing film layer. The skin-protective agent is on the side of the article that comes into contact with the person using (wearing) the article.

The skin-protective agent may be encapsulated in an encapsulation system. The encapsulation system may be a bilayer membrane system (e.g. liposomes, produced with a phospholipid, such as lecithin), a micelle or other lipid or non-lipid based single-layer membrane systems, or a microcapsule. Microcapsules may be based on gelatin, shea butter gum, polyacetyl urea (e.g. polyoxylmethylene), or combinations thereof. The encapsulation system can aid in immobilisation on the internal surface of the elastomeric article and delivery of the probiotic and/or prebiotic to the user's skin.

In the following we describe coating application first, followed by incorporation into a film-forming composition. In a later section, additional details of the methods used to incorporate the skin-protective agent are described.

Skin-Protective Agent Provided as a Coating on the Elastomeric Film

In one example, the skin-protective agent can be incorporated into the elastomeric article by the application of the skin-protective agent or a coating composition comprising the skin-protective agent. This forms a coating layer on the elastomeric article. Details of suitable coating compositions are set out further below in a section describing coating techniques.

In such embodiments, the coating layer that remains on the inner surface of the elastomeric film may comprise the skin-protective agent only, or it may comprise skin-protective agent and one or more additional components selected from the group consisting of coating polymers, dispersing agents, emulsifiers, solubilisers, rheology modifiers, wetting agents, emollients, skin conditioning agents, a humectant, a biocide, a preservative, silicone, fragrance and a pH adjustor.

In some examples herein, the coating composition comprises about 3% of the skin-protective agents, 5.6% of other coating components, and the balance water. Thus, on removal of the water, the skin-protective agents constitute about 35% of the dried coating. The coating layer containing 35% skin protective agents constitutes about 11% by weight (dry weight) of the 4 g elastomeric article, based on a pickup of a typical amount of 1.5 ml of the coating solution onto a medium sized glove. The amount of coating pickup may be as little as 0.1 mL, and may be as higher than 1.5 ml. From this example, variations may be made accounting for lower and higher amounts of skin-protective agent in the coating composition, and the application of a lower or higher amount of the coating composition during manufacture of the gloves.

Consequently, the total weight of the (dried) coating containing a skin-protective agent (i.e. following removal of solvent such as water) may be between 0.001 and 75% by weight of the elastomeric article. The weight percentage of the article taken up by the coating layer containing the skin-protective agent in the final product (i.e. a dried weight) may be a minimum of 0.001%, 0.01%, 0.05%, 0.1%, 0.5%, 1%, 1.1%, 1.2%, 1.3%, 2.5%, 5%, 7.5% or 10% by weight (based on the total article weight). The weight percentage of the article taken up by the coating containing the skin-protective agent may be less than 50%, 30%, 25%, 22.5%, 20%, 17.5%, 15%, 12.5%, 10%, 7.5%, 5%, 4% or 3% by weight of the total article weight. Any minimum and maximum can be combined to form a range, provided that the maximum is greater than the minimum, such as a range of between 0.01% and 50%, or 0.1% and 25%.

In some embodiments, the total amount of the skin-protective agent in the coating layer is at least 5% by weight of the coating layer. For example, the total amount of skin-protective agent in the coating layer is from about 5% to 100%, or at least about 10%, 20%, 25%, 30% or at least about 40% by weight of the coating layer. The amount may be a maximum of 80%, 60%, 50% or 40%, provided that the lower amount is less than this maximum. The balance may be made up of other coating components.

In the example of a glove, weighing approximately 4 g (prior to coating), the coating composition may be applied in a typical amount of at least 0.001 mg of dried skin-protective agent, such as at least 0.005 mg, at least 0.01 mg, at least 0.05 mg, at least 0.1 mg, at least 0.5 mg, or at least 1 mg of dried skin-protective agent. In preferred embodiments, the glove coating composition may be applied in an amount of from about 4 mg to 1000 mg of dried skin-protective agent, equivalent to 0.1% to 25% by weight of the total glove weight. Expressed another way, the volume of coating composition containing skin-protective agent picked up by a glove is about 0.1 mL or more, preferably about 0.5 mL to about 5 mL per glove. These amounts also serve as a useful guide for a range of other articles, although the amounts may vary depending on the size of the article.

The coating composition comprising the skin-protective agent is preferably free of gelling agents. The coating is preferably a non-gelled coating. The coating comprising the skin-protective agent is preferably hydrogel free. The coating comprising the skin-protective agent is preferably free of alginates, such as sodium alginate.

Skin-Protective Agent within the Elastomeric Film

Another technique for incorporating the skin-protective agent into the elastomeric film is by way of including the skin-protective agent(s) in the latex composition (elastomeric film-forming composition) that is used to form a layer of the elastomeric article.

In embodiments where the skin-protective agent is incorporated into the elastomeric film, the elastomeric article may comprise a multilayer film having at least 2 layers. The skin-protective agent is incorporated into the internal film layer which is in contact with the user's skin when the article is in use. The multilayer film optionally comprises a barrier layer between the internal film layer incorporating the skin-protective agent and the antimicrobial agent on the external surface of the article. In other embodiments, the article may comprise a single layer film, and the antimicrobial agent may form or be present in a coating on the surface of the elastomeric film, with or without a coating layer (forming a barrier layer) therebetween.

Depending on the manner of inclusion of the skin-protective agent into the elastomeric film-forming composition, the probiotic and/or prebiotic may migrate to the internal surface of the elastomeric article upon storage, thus providing the beneficial properties of the substance(s) to the internal surface of the elastomeric article in contact with the user's skin. The skin-protective agent may alternatively remain throughout the layer of elastomeric film (matrix), but at a concentration or in an amount such that the probiotic and/or prebiotic can provide beneficial properties to the user's skin.

Barrier Layer

The elastomeric article optionally comprises a barrier layer between the antimicrobial agent on the external surface of the article and the skin-protective agent on the internal surface of the article. This layer functions as a barrier layer and does not contain any antimicrobial agents or skin-protective agents. The barrier layer is advantageous as it is capable of preventing or reducing the migration of any antimicrobial agents or any skin-protective agents across the layer.

The barrier layer may constitute a film layer or a coating layer, such that the barrier layer provides separation between the part of the article that contains or bears the antimicrobial agent, and the part of the article that contains or bears the skin-protective agent.

The barrier layer may be between 0.002 mm and 2 mm in thickness.

Barrier Film Layer

In some embodiments, the barrier layer is in the form of a layer of elastomeric film. The barrier film layer resists penetration and contact by the antimicrobial agent with the user's skin. In addition, the barrier film layer resist penetrations and contact of the antimicrobial with the skin-protective agent on the internal surface of the article.

In embodiments where the elastomeric film of the elastomeric article is a single-layer film, the single-layer elastomeric film makes up the barrier film layer separating the antimicrobial agent and the skin-protective agent. In these embodiments, each of the antimicrobial agent and skin-protective agent are applied as coatings on opposite sides of the barrier film layer.

In embodiments where the elastomeric film is a multilayer film, at least one of the film layers of the multilayer film makes up the barrier film layer separating the antimicrobial agent and the skin-protective agent. By way of example, in an elastomeric film comprising 2 layers, the external film layer may incorporate an antimicrobial agent and the internal film layer may be the barrier film layer. In this case, the skin-protective agent is included in a coating layer on the internal surface of the article (i.e. on the internal film layer).

The barrier film layer may be between 0.005 mm and 2 mm in thickness. The minimum thickness in some embodiments corresponds to a fraction of the total film thickness—for example, it may be a minimum of 10% of the total film thickness, based on the thickness of that barrier film layer as a percentage of the total thickness of the multilayer film. The maximum thickness corresponds to the total elastomeric film thickness, given that the antimicrobial agent and skin protective agent may form very thin coatings on a single elastomeric film layer, which constitutes the barrier film layer.

The barrier film layer is preferably an elastomeric film-forming polymer that may be selected from rubber and synthetic rubber (natural or synthetic), nitrile butadiene, self-crosslink nitrile butadiene, polyurethane, polyisoprene, polychloroprene, polyvinyl chloride, polybutadiene, polyacrylonitrile butadiene rubber, polystyrene butadiene rubber, fluoroelastomers, butyl rubber, acrylic polymers (including acrylic diene block copolymers), polyvinylpyrrolidone, polysiloxane and copolymers of these with other polymers/monomers (random copolymers, block copolymers or otherwise). Modified forms of these polymers or copolymers (e.g. polymers containing additional substituents such as carboxylate, sulfonate, halide or other substituents) are also encompassed. The polymers may be carboxylated or non-carboxylated.

The barrier layer may comprise a filler. While such fillers are not essential for the barrier layer, they can provide improved barrier properties between the anti-microbial and the skin-protective agent. The filler can aid in resisting or preventing the migration of the antimicrobial agent to the skin-contacting side of the article (e.g. the donning side).

The barrier layer (with or without filler) also resists or prevents the invasion of microbes to the skin-contacting side of the article.

The filler, when present, is preferably a lamellar filler. Lamellar fillers are fillers having a lamellar, layered or platelet form. Lamellar fillers maintain their shape because they do not exhibit any crosslinking with the elastomer that forms the elastomeric film. Examples of lamellar fillers include lamellar minerals, clays, fibre and similar, including lamellar talc, kaolin and mica. The fillers may be conventional lamellar fillers with a lamellarity index of about 2-8, or in some embodiments a high lamellar filler with a lamellarity index of about 9-14 is used. Fillers with a higher lamellarity index have a higher surface area compared to the platelet thickness. Such high lamellar fillers can strengthen the physical barrier film layer. This improves the efficacy of the elastomeric article as a physical barrier against pathogens, and can further resist any potential migration of antimicrobial agents on the external surface of the article to the internal surface of the article. In alternative embodiments, a non-lamellar filler may be used, although these are do not have the benefit of the lamellar fillers in terms of restricting or slowing down the diffusion of liquids and gases across the film. Examples of non-lamellar fillers may include fibre, cellulose, calcium carbonate and barium sulphate.

Barrier Coating Layer

In some embodiments, the barrier layer is a coating layer present between the part of the elastomeric article containing the antimicrobial agent and the part of the elastomeric article containing the skin-protective agent.

In these embodiments, the elastomeric film of the elastomeric article is typically a single-layer film but may alternatively be a multilayer film. The barrier coating layer may be present between a film layer containing the antimicrobial agent and a coating layer containing the skin-protective agent. Alternatively, the barrier coating layer may be present between a film layer containing the skin-protective agent and a coating layer containing the antimicrobial agent.

The barrier coating layer may be between 0.002 mm and 0.050 mm in thickness. For example, the barrier coating layer may be between 0.002 mm and 0.010 mm in thickness, such as about 0.003 mm or about 0.004 mm in thickness.

The barrier coating layer is preferably in the form of a polymer coating layer. The coating composition may comprise a coating polymer or polymer emulsion, such as polyacrylic emulsion, a polyurethane emulsion, a silicone emulsion, paraffin wax, polyethylene waxes, or a combination thereof.

No Barrier Layer

The barrier layer is a physical barrier that separates the part of the elastomeric article containing the antimicrobial agent and the part of the elastomeric article containing the skin-protective agent. This prevents or reduces the likelihood of the antimicrobial agent and skin-protective agents from interacting with each other, thereby allowing each component to independently act more effectively. However, it is also possible to produce gloves without a barrier layer. For example, the barrier layer may be omitted if the antimicrobial agent and the skin-protective agents are immobilized within the respective parts of the article (e.g. a layer of elastomeric film or a coating) that contains these agents, without migration of the agents to other parts of the article.

Elastomeric Articles

Examples of elastomeric articles that benefit from having an antimicrobial agent on the external surface and a skin-protective agent on the internal surface include wearable articles, including gloves (encompassing disposable gloves, surgical gloves, examination gloves, industrial gloves, laboratory gloves, irradiation gloves, clean room gloves for electronic industries, gloves for food contact and food processing and biotechnical application, household gloves, supported gloves and so forth), finger cots, footwear (such as foot covering, socks, booties), medical dressings and the like. The articles are suitably disposable elastomeric articles—being of light weight and low cost, suitable for disposable after a period of use. The articles may be thin film articles. The articles may be dipped articles (i.e. articles produced from a dipped elastomeric film, composition may be applied by dipping or otherwise). The former used for the dipping process is shaped in accordance with the type of article—hand-shaped for a glove, finger-shaped for finger cot, or foot-shaped for footwear. The articles are not limited to dipped articles and also encompass articles such as extruded elastomeric articles and medical dressings and the like.

The thickness of the elastomeric film (including any coating applied to the article) can, for example, be in the range 0.01-3.0 mm, such as 0.01-2.0 mm, 0.01-1.0 mm, 0.01-0.3 mm, 0.02-0.2 mm, 0.05-0.10 mm, 0.03-0.08 mm, or 0.05-0.08 mm (for thin or disposable gloves and articles), and 0.2-3.0 mm for thick gloves and articles. The thickness is suitably measured as an "average thickness" for the article. In the case of gloves, the thickness is measured using an average of the thickness measurements taken at the cuff, palm and finger locations, according to ASTM D6319. The finger thickness is measured 13 mm+/−3 mm from the fingertip; the palm thickness is measured at the centre of the palm, and the cuff thickness is measured at 25 mm+/−5 mm from the cuff edge. Thickness measurements for any elastomeric articles are taken in accordance with the procedure specified in ASTM D3767-03 (Reapproved 2014).

The elastomeric articles as described herein substantially retain the desirable elastomeric properties of the underlying elastomeric films, in spite of the inclusion of the antimicrobial agent and the skin-protective agent. The presence of an antimicrobial agent and/or the skin-protective agent can in fact result in desirable changes to some properties of the film. In some embodiments, the presence of the antimicrobial agent and the skin-protective agent provides excellent softness and low modulus. The softness may be greater than a comparative product without the antimicrobial agent. The softness may be greater than a comparative product without the antimicrobial and skin-protective agents. These properties may act to minimise hand fatigue, thus improving productivity of the wearers with less muscle effort at work.

The modulus at 500% of the articles of some embodiments is less than 15 MPa. For example, the modulus at 500% may be up to 10 MPa, or between 2 and 10 MPa, or up to 8 MPa, or up to 6 MPa. In some embodiments, the modulus is higher than a comparative product without the antimicrobial agent, indicating a higher softness. The modulus may be higher than a control or comparative product that does not contain the antimicrobial agent, by a factor of about 4% to up to 80%, such as 4% to about 50%, as demonstrated in the Examples.

The modulus at 300% elongation of the articles of some embodiments is less than 10 MPa. For example, the modulus may be between 1 and 10 MPa, between 1 and 5 MPa, or between 1 MPa to 4 MPa.

It is noted that the modulus values (at 300% and 500% elongation) are based on unaged films. The ranges indicated may also apply to aged films.

In some embodiments, the elastomeric article has a tensile strength of at least 8 MPa (e.g. from 8 MPa to 50 MPa, at least 14 MPa, or from 14 MPa to 25 MPa).

When comparing the tensile strength of the article of the present application against that for the same article without the antimicrobial agent, it is desirable for there to be minimal change. In some embodiments, the tensile strength does not vary from that of a comparative article without the antimicrobial agent by more than 50%, 40%, 30%, 20% or 15%. With reference to the examples shown herein, the tensile strength of one exemplified product containing 1 phr of ZPT antimicrobial had a tensile strength of 16.17 MPa, and another product containing 4 phr of ZPT had a tensile strength of 21.29 MPa, which were 13% less and just under 15% greater than that of the control product (21.29 MPa), respectively. These values are within 15% (plus or minus) of the control.

In some embodiments, the elastomeric article has an elongation to break of at least 200% (e.g. between 200% and 1000%, between 300% and 1000%, between 400% and 1000%, between 500% and 1000%, from 600% to 1000%, or from 700% to 1000%). In some embodiments, the elastomeric article has an elongation to break of at least 500%.

The elongation at break of the products of the present application may be slightly lower than that of a comparison or control product that is free of the antimicrobial agent. The elongation at break is preferably not more than 20% less than that of a control product that is free of the antimicrobial agent, preferably not more than 15% less. The elongation at break may in some instances be higher than that of the comparison product, potentially up to 10, 15 or 20% higher.

The elastomeric article may have one, two or all three of the modulus, tensile strength, and elongation at break values within the ranges indicated above.

The calculations of weight, thickness, modulus, tensile strength and elongation may be based on a sample of at least 10 articles (e.g. gloves or finger cots).

Elastomeric Film-Forming Composition

In the following section the components of the elastomeric film-forming composition used to produce the or each layer of the elastomeric film are described. As noted above, one or more layers of the elastomeric article may contain (a) an antimicrobial agent, or (b) the skin-protective agent. There may be layers that are free of those agents, such as a barrier layer of the film (when present). Accordingly, the following description applies to any of these layers, with the proviso that the composition may also contain an antimicrobial agent or a skin-protective agent, depending on the embodiment and the layer being formed.

The elastomeric film-forming composition from which the elastomeric film is made comprises the elastomer and one or more cross-linking agents in a liquid medium. The liquid medium is typically water.

The total solids content of the elastomer component of the elastomeric film-forming composition is from 5% to 60% by weight of the composition. The percentage of total solids content (TSC %) can vary within this range. In some embodiments, the total solids content is about 5% to 50%, 10% to 50%, 20% to 50%, or 5 to 40%.

The elastomeric film may be a self-supported or unsupported film. A self-supported or unsupported film is a film that exists without other structural components or layers that the film is adhered to or attached to.

It is also common in the art to use the expression "latex" or "rubber" to refer to any elastomer in a general sense. Accordingly, particularly in the examples which follow, it should be understood that these terms have been used as short-hand to refer to the elastomer of the dipping composition.

Elastomers

Elastomer-forming polymers include natural rubber and synthetic elastomer-forming polymers, which can be cross-linked to produce elastomeric films. The polymer may be a single polymer or a combination of two or more polymers. The polymer may be a homopolymer or a copolymer, or a blend of polymers/copolymers.

The elastomer-forming polymers may be selected from rubber (natural or synthetic), nitrile rubber, silicone rubber, polyvinyl chloride, polyethylene, polypropylene, polyurethane, polyisoprene, polychloroprene, polybutadiene, polyacrylonitrile butadiene rubber, polystyrene butadiene rubber, fluoroelastomers, butyl rubber, acrylic polymers (including acrylic diene block copolymers), and copolymers of these with other polymers/monomers (random copolymers, block copolymers or otherwise). Modified forms of these polymers or copolymers (e.g. polymers containing additional substituents such as carboxylate, sulfonate, halide or other substituents) are also encompassed. The polymers may be carboxylated or non-carboxylated.

One notable example of a synthetic elastomer-forming polymer is polyacrylonitrile butadiene. This may be carboxylated or non-carboxylated. This may be provided as a mixture of carboxylated nitrile latex and nitrile butadiene rubber. Another example of a suitable elastomer-forming polymer is self-crosslink nitrile butadiene latex.

Carboxylated refers to the presence of carboxylate (carboxylic acid or ester) groups on the polymer chain. Carboxylation may be achieved by forming the polymer with a monomer containing carboxylate groups, or through grafting carboxylate groups to a polymer. As examples of suitable carboxylated polymers, reference is made to PCT/AU2014/000726 and PCT/AU2014/000727, the entirety of each being incorporated into this specification by reference.

In the art of the present invention, it is common to refer to the amount of the elastomer as being 100 phr (per hundred parts "rubber"), and for the relative amounts of the remaining components of the elastomeric composition to be calculated as a number of parts compared to the 100 phr of the elastomer, by weight. Thus, for an amount of cross-linking agent that is 1/100th that of the elastomer in the composition by weight, the amount of cross-linking agent is referred to as 1.0 phr.

Cross-Linking Agents

The elastomeric film-forming composition comprises a cross-linking agent. Elastomer-forming polymers can be cross-linked with one or more cross-linking agents to produce the elastomeric film. Various types of cross-linking agents can be used. Cross-linking agent classes include ionic cross-linking agents and covalent cross-linking agents. The cross-linking agent or agents used in the production of the elastomeric film may be selected from ionic cross-linking agents, covalent cross-linking agents, and combinations thereof. The selection will depend on various factors including the properties of the film desired and the choice of elastomer.

Ionic cross-linking agents include metal oxide cross linking agents (such as zinc oxide and magnesium oxide), peroxides (such as 1,1-di(t-butylperoxy)-3,3,5-trimethylcyclohexane, which can be purchased under the trade name Trigonox 29-40B-pd), trivalent metal-based cross-linking agents, such as sodium aluminate. The trivalent metal cross-linking agent may be solubilized to produce a negatively charged multivalent metal complex ions.

Covalent cross-linking agents include organic cross-linking agents, sulphur and/or sulphur donors, and combinations thereof. The elastomeric film-forming composition may contain sulphur, or it may be sulphur-free.

Sulphur may be added in the form of elemental sulphur. Sulphur donors are another way of providing sulphur cross-linking. Sulphur donors release sulphur, or act with sulphur-containing compounds, to accelerate sulphur-based covalent cross-linking of the elastomer-forming polymer. These sulphur donors may also be referred to as accelerators. Examples of suitable sulphur donors include the carbamates such as thiocarbamates (e.g. zinc dibutyl dithiocarbamate (ZDBC), Zinc diethyl dithiocarbamate (ZDEC); Zinc dimethyl dithiocarbamate (ZDMC); thiurams (e.g. tetraethylthiuram disulfide (TETD), Tetramethylthiuram disulphide (TMTD)); Dipentamethylene thiuram tetrasulfide (DPTT); Dipentamethylene thiuram hexasulfide (DPTH); Dipentamethylene thiuram hexasulfide; thiourea (Ethyl thiourea (ETU) and diphenylthiourea (DPTU); thiazoles (e.g. Mercapto Benzothiazoles (MBT), Mercapto Benzothiozole disulphide (MBTS), zinc 2-mercaptobenzothiazole (ZMBT)); guanidines (e.g. Diphenylguanidine (DPG)) and aldehyde/amine-based sulphur donors (e.g. hexamethylenetetramine). Other examples are well known in the art and can be obtained from various publicly available sources.

In broad terms, any amount of cross-linker may be used, as required for the final article properties. Thus, the total amount of cross-linking agents in the composition may be between 0.01 and 14 phr. The total cross-linking agent amount may be within one of the following ranges: 0.01-8 phr, 0.1-6 phr, 0.1-5 phr, or 0.01-1.0 phr.

The amount of ionic cross-linking agent may be between 0.0-4.0 phr, such as 0.01-4.0 phr. The amount is preferably lower still, at 0.01-3.0 phr, or 0.01-2.0 phr, 0.01-1.0 phr or 0.01-0.5 phr.

The amount of sulphur may be between 0.0-5.5 phr. The amount may be lower still, at 0.0-3.5 phr, such as 0.01-3.0 phr, 0.01-2.0 phr, 0.01-1.5 phr, 0.01-1.0 phr or 0.01-0.5 phr.

The amount of sulphur donor (e.g. accelerator) may be between 0.0-2.0 phr, such as between 0.1-1.5 phr, 0.1-1.0 phr, 0.2-1.0 phr, 0.3-2.0 phr, 0.3-1.5 phr or 0.2-0.6 phr.

Other Components of the Elastomeric Film-Forming Composition

The elastomeric film may further comprise one or more of the following conventional components of an elastomeric film-forming composition: plasticizers, anti-oxidants, anti-ozonants, stabilisers such as pH stabilisers, pH adjustors (e.g. agents for increasing the pH, such as potassium hydroxide, ammonia, sodium hydroxide, or mixtures thereof), surfactants, emulsifiers, antioxidants, polymerisation initiators, pigments, fillers, opacifying agents, colourising agents, rubber reoderants/deoderants, wetting agents, defoamers and sensitisers. These agents, and the amounts and examples thereof, are as described in PCT/AU2014/000726 and PCT/AU2016/050308; the entirety of each is incorporated by reference.

Optional antimicrobial agent in the elastomeric film-forming composition

In some embodiments, the elastomeric film-forming composition from which a layer of the elastomeric film is made contains one or more antimicrobial agents. In embodiments where the elastomeric article comprises a barrier film layer, another layer of the film will form the barrier film layer, which is free of the antimicrobial agent (and free of the skin-protective agent). In embodiments where the elastomeric article is a dipped article, this is typically the first film layer, which ends up on the outwardly-facing surface of the article when the article is inverted by stripping from the former.

The antimicrobial agent in the first elastomeric film-forming composition may be a pyrithione antimicrobial agent.

The antimicrobial agent may be present in the elastomeric film-forming composition at a concentration of from about 0.01 phr to 20 phr, when incorporated through this technique. In some embodiments the maximum amount is 15, 10, 5 or 3 phr. In some embodiments, the minimum amount (when present) is 0.01, 0.05, 0.1, 0.5, 1.0 or 2 phr. Any maximum and minimum cam be combined to form a range. Suitable ranges include 0.05 to 15 phr, 0.1 to 10 phr, 0.5 to 5 phr, and 2 to 3 phr.

Optional Skin-Protective Agent in the Elastomeric Film-Forming Composition

In some embodiments, the elastomeric film-forming composition from which a layer of the elastomeric film is made contains one or more skin-protective agents, selected from probiotics and/or prebiotics. In embodiments where the elastomeric article is a dipped article, this is typically the final film layer (final elastomeric film dipped layer), which becomes the inwardly-facing surface of the article when the article is inverted by stripping from the former. By way of example, for multilayer films having 2 layers, the elastomeric film-forming composition containing the skin-protective agent(s) would be the second elastomeric film-forming composition and is used to form the second film layer. For multilayer films having 3 layers, this composition would form the third film layer.

In some embodiments, the skin-protective agent comprises a probiotic, and the probiotic is a thermophile, such as a hyperthermophile. These classes of probiotics are preferred when incorporated into the film-forming composition, since this composition is maintained at an elevated temperature during dipping and drying, and the probiotic preferably withstands these heat conditions.

The probiotic may be present in the elastomeric film-forming composition at a concentration of at least about 0.001 phr, preferably 0.01 to 50 phr. These amounts apply to the total amount of all probiotics in the film-forming composition.

The skin-protective agent may additionally, or alternatively, contain a prebiotic. The prebiotic may be present at a concentration of at least about 0.001 phr, preferably 0.01 to 50 phr (i.e. total for all prebiotics).

When the skin-protective agent(s) is present in the film-forming composition, the amount of skin-protective agent added to the latex composition will depend on the type of elastomer and cross-linking agent that is used. In some embodiments, the total amount of skin-protective agent in the elastomeric film-forming composition in an amount of at least about 0.001 phr, preferably from about 0.01 to about 50 phr. In some embodiments the maximum amount is 40, 30, 20, 15, 10, 5 or 3 phr. In some embodiments, the minimum amount (when present) is 0.01, 0.05, 0.1, 0.5, 1.0 or 2 phr. Any maximum and minimum can be combined to form a range. Suitable ranges include 0.05 to 20 phr, 0.1 to 10 phr and 0.5 to 5 phr.

Optional Barrier Film Layer Components

In some embodiments, a barrier film layer is produced from the elastomeric film-forming composition. The barrier film layer-forming composition is free of antimicrobial agents and skin-protective agents. The barrier film layer composition may optionally contain a lamellar filler. The amount of lamellar filler is preferably at least 0.05 phr, and preferably a maximum of 70 phr. In some embodiments the maximum amount is 60, 50, 40, 30, 20, 15, 10, 5 or 3 phr. In some embodiments, the minimum amount (when present) is 0.05, 0.1, 0.5, 1.0, 1.5 or 2 phr. Any maximum and minimum cam be combined to form a range. Suitable ranges include 0.5 to 20 phr, 0.1 to 10 phr and 0.5 to 5 phr.

Formulation for Elastomeric Film-Forming Compositions of Embodiments of the Invention In some embodiments, the elastomeric composition used to form a film layer of the elastomeric article comprises:
(a) A dispersion of a film-forming elastomer (such as nitrile, natural rubber, self-crosslinking nitrile butadiene latex, polychloroprene, polyisoprene, polyurethane, polyacrylic, polyvinylpyrrolidone, polystyrene butadiene rubber, fluoroelastomer, butyl rubber, polyvinyl chloride, polybutadiene, polysiloxane, or mixtures thereof);
(b) Optionally an antimicrobial agent, or optionally a skin-protective agent, or optionally a lamellar filler (as mutually exclusive alternatives);
(c) A pH adjustor (such as potassium hydroxide, ammonia, sodium hydroxide or a mixture thereof);
(d) One or more crosslinking agents (such as sulphur, sulphur donor, metal oxide, ionic crosslinking agent and the like);
(e) Optionally an accelerator (such as dithiocarbamate, thiuram, mercapto and the like); and
(f) Optionally one or more additional components selected from anti-oxidant, anti-ozonant, wetting agent, emulsifier, defoamer, stabilizer, rubber deodorant, colour pigment, opacifier and the like.

In some embodiments, the elastomeric composition is accelerator-free. In some embodiments, the crosslinking agent in the elastomeric composition is sulphur-free.

Preparation of the Elastomeric Article

The elastomeric film-forming composition having the desired components is formed into the shape of the desired article, and then cured. Curing is used in a general sense to refer to the stage during which cross-linking is performed. Such curing conditions are as known in the art.

For dipped elastomeric articles, the elastomeric film is suitably prepared by a dipping process.

In brief, in one embodiment of the invention, the method for the manufacture of the elastomeric article may comprise:
dipping a mould into a coagulant composition,
dipping the coagulant-dipped mould into a first elastomeric film-forming composition for producing a first layer of elastomeric film on the mould;
incorporating an antimicrobial agent into the coagulant composition and/or the first elastomeric film-forming composition, to result in the incorporation of the antimicrobial agent into the first film layer that defines a first surface of the elastomeric film;
dipping the mould with the first layer of elastomeric film into a second elastomeric film-forming composition that is free of antimicrobial agent and free of skin-protective agent to produce a barrier film layer;
optionally dipping the mould into additional elastomeric film-forming compositions prior to or following dipping into the second elastomeric film-forming composition; and
either (a) dipping a mould comprising the layers of elastomeric film into a third elastomeric film-forming composition comprising a skin-protective agent, or (b) applying a coating composition comprising the skin-protective agent onto the layers of elastomeric film, so that the skin-protective agent is present in or on a second surface of the elastomeric film.

Whilst the above series of steps outlines one technique for producing the elastomeric articles, variations to this process may be made as described in detail below. It should be understood that additional variations may be made to this process as known or described in the art. The steps in the manufacture of an elastomeric film or article may be as generally described in PCT/AU2014/000726 and PCT/AU2014/000727, which are incorporated by reference.

By way of example, the method may comprise:
dipping a mould into a coagulant composition,
dipping the coagulant-dipped mould into a first elastomeric film-forming composition for producing a first layer of elastomeric film on the mould;
incorporating an antimicrobial agent into the coagulant composition and/or the first elastomeric film-forming composition, to result in the incorporation of the antimicrobial agent into the first film layer that defines a first surface of the elastomeric film;
optionally dipping the mould into additional elastomeric film-forming compositions prior to or following dipping into the second elastomeric film-forming composition; and
either (a) dipping a mould comprising the layers of elastomeric film into a third elastomeric film-forming composition comprising a skin-protective agent, or (b) applying a coating composition comprising the skin-protective agent onto the layers of elastomeric film, so that the skin-protective agent is present in or on a second surface of the elastomeric film.

Optional step (a) Dipping the former into a coagulant containing metal ions in solution Dipping the former into a coagulant composition is an optional step in the process for the production of dipped elastomeric articles. Charged ions in the coagulant form a charged ion coating on the former that can assist in controlling the amount of elastomeric film-forming composition that will subsequently remain on the surface of the former after dipping into the film-forming composition, through charge interactions. If the antimicrobial agent is added via the coagulant dipping, then a coagulant dipping step is performed, with an antimicrobial agent in the coagulant composition.

The coagulant comprises charged ions, such as metal salt ions. Examples of such metal salt ions are sodium, calcium, magnesium, barium, zinc, and aluminium. Preferred metals are the multivalent metals. The counter ions may be halides (such as chloride), nitrate, acetate or sulphate, amongst others. In the case of calcium ion-containing coagulants, the calcium ions can be provided as a solution of calcium nitrate or calcium chloride. Other optional components of the coagulant may include an anti-microbial agent (for embodiments where the antimicrobial is introduced through the coagulant), wetting agents (such as fatty alcohol ethoxide or other suitable surfactants), anti-tack agents, anti-foaming agents and/or mould release agents (such as silicon emulsions), polymer release agents and metallic stearates (such as zinc, calcium and potassium stearates).

The concentration of metal salt, as the ion source, in the coagulant can broadly be in the range of 0.0-50% by weight of the coagulant composition, depending on the desired thickness of the elastomeric film layers and the number of layers to be applied (i.e. one layer or two or more layers). In the case of thinner layers, the metal salt concentration is suitably in the range of 0.0-20%, 0.0-15%, 0.0-12%, 1.5-20%, 1.5-15%, 1.0-10%, 1.5-10%, 4-10%, 5-10%, 5-35%, 10-30%, 7-40%, 8-50% and 5-45%. The amounts of other optional components such as wetness and anti-tack agents are dependent on the properties desired through the use of these agents and will vary accordingly.

In some embodiments, the coagulant composition contains an antimicrobial agent, or a mixture of antimicrobial agents as described above. Of the antimicrobial agents described, those best suited for inclusion in the coagulant composition are phenolic compounds, heterocyclic compounds and quaternary salt compounds, such as 2-phenylphenol, piroctone olamine or a combination thereof. In such embodiments, the antimicrobial agent is present in the coagulant composition in a (total) amount of at least about 0.001% by weight. The amount of antimicrobial agent in the coagulant composition may be a maximum of about 50% by weight. The minimum amount may be at least 0.01%, 0.1%, 0.5% or 1% by weight. The maximum amount may be 40%, 30%, 20% or 10% by weight of the composition. Any minimum and maximum can be combined without limitation to form a range, one useful range being 0.01% to 10%.

The antimicrobial agent in such embodiments may be incorporated into the coagulant through addition of the antimicrobial agent (neat, as a water-soluble liquid or water soluble solid, or as an emulsion, solution or dispersion) into a coagulant composition, or through formulation of the coagulant with the antimicrobial agent as one component thereof. Once the coagulant coating is applied onto the former through dipping, and the first layer of elastomeric film-forming composition is applied on the coagulant-coating layer, the components of the coagulant including the antimicrobial agent penetrate partially into the film-forming composition layer, so as to be present on/within a region of that elastomeric film layer that contacts the coagulant. In embodiments where the elastomeric article comprises a barrier film layer, it is preferred in this case for a second film layer to be applied to form the barrier layer between the first film layer containing the coagulant-supplied antimicrobial agent. The antimicrobial agent applied through the coagulant dipping step may not penetrate or diffuse far into the first film layer, and may not diffuse into any subsequently-applied film layers, when added via the coagulant composition. In this embodiment, the second film layer applied after the first may constitute the barrier film layer. Nevertheless, it is possible to produce a product with antimicrobial agent in the coagulant layer, a single elastomeric film as the barrier film layer (particularly if the single film layer contains lamellar filler to prevent migration of the antimicrobial agent through that layer), and an outer coating layer of the skin-protective agent.

Optional Step (b) Drying or Partially Drying the Coagulant-Dipped Former

If the former is dipped into a coagulant, following this step the former is dried or partially dried.

Step (i) Dipping the Former into a First Elastomeric Film-Forming Composition to Produce a First Layer of Elastomeric Film-Forming Composition on the Mould The former is dipped into a composition for producing an elastomeric film, embodiments of which have been described in detail above. The film-forming composition of the first dip (the "first elastomeric film-forming composition") may in some embodiments contain the antimicrobial agent, or in other embodiments may be free of antimicrobial agent and free of skin-protective agent so as to form a barrier film layer, depending on the particular layer structure being produced.

The former is in the dipping tank for an amount of time (a dwell time) to ensure the former is evenly coated, but not so long as to develop a thicker coating than necessary.

The temperature of the composition into which the former is dipped is generally within the range of 10° C. to 60° C. The temperature may be modified or controlled to be within a narrower temperature range if the first film-forming composition contains any components that are sensitive to heat.

If a single film-layer article is produced, the next step performed is step (v). In embodiments where the elastomeric article comprises a barrier layer, which is a barrier film layer, the first elastomeric film-forming composition is free of antimicrobial agents and is free of probiotics and/or prebiotics.

Step (ii) Drying or Partially Drying the First Layer of Elastomeric Film-Forming Composition on the Former Where a second (and optionally further) film layer is being applied, the first layer is dried or partially dried prior the next stage of dipping. Conventional drying conditions as is known in the art is used in performing this step, such as those described in the PCT publications referred to previously.

Step (iii) Optionally Dipping the Former Coated with the Dried or Partially Dried First Layer of Elastomeric Film-Forming Composition into a Second Elastomeric Film-Forming Composition to Produce a Second Layer of Elastomeric Film-Forming Composition on the Former This step is optional, and is present when multilayer film articles are produced. The temperature, dwell time and total solids content for the elastomeric film-forming composition used to produce the second layer of the glove (i.e. the second elastomeric film-forming composition) may be the same as for the first dip, or they may be different. The second elastomeric film-forming composition into which the former is dipped may be the same as that for the first dip, or it may be different.

In embodiments where the elastomeric article comprises a barrier film layer, and where the first elastomeric film-forming composition contains an antimicrobial agent, the second film-forming composition is free of antimicrobial agents and is free of probiotics and/or prebiotics, so as to produce a barrier film layer.

In some embodiments, the second elastomeric film-forming composition contains a skin-protective agent. In these embodiments, the first elastomeric film-forming composition is free of antimicrobial agents and is free of probiotics and/or prebiotics.

Step (iv) Optionally Repeating the Drying or Partial Drying Step (ii) and the Further Dipping Step (iii)

This step is optional, and is present when multilayer film articles are produced. The number of film layers may be 2, 3 or more in multilayer film articles. In each subsequent dipping stage, the choice of film-forming composition will be selected to produce the required layered structure desired. Accordingly, in one embodiment, a third elastomeric film-forming composition is used to produce a third elastomeric film layer. This third elastomeric film-forming composition may be one containing a skin-protective agent, so as to produce a film layer that comprises a skin-protective agent. In such cases, the skin-protective agent is preferably thermally stable. If the skin-protective agent present in the film-forming composition is thermally stable, the dipping temperature should be controlled appropriately (e.g. by setting a maximum dipping temperature of, for example, 30° C.). The probiotic choice should also be made depending on its stability during the required dipping conditions. In an alternative embodiment, the composition may be free of antimicrobial and free of skin-protective agents, so as to produce another standard film layer (or a barrier film layer, when present). In this instance, the skin-protective agent may be applied through a coating composition, as described below.

Step (v) Optional Additional Steps Prior to Curing

Further steps can be taken to fine-tune the manufacture of the elastomeric film or article. The details of some optional steps that may be performed prior to curing are as described in the PCT publications referred to above. In brief, the film or article can be pre-leached to remove extractable components, there may be a coating material applied before/after beading/cuffing is optionally performed. Some option steps that may be conducted at this stage are described below under the headings (v-1) and (v-2).

Step (v-1) —Pre-Leaching

In some embodiments, a leaching step (described as pre-leaching) is performed following the elastomeric film composition dipping steps, and prior to curing. The elastomeric film on the former at this time contains an antimicrobial agent, and in some embodiments, the skin-protective agent is to be applied through a subsequent coating stage (either before or after curing). It is desirable in such embodiments to perform a leaching step to remove or wash away excess chemical residues. Excess antimicrobial may be one of the chemical residues that may be washed away. Without the leaching step, the antimicrobial agent may contaminate the composition containing the skin-protective agent, and if the skin-protective agent includes a probiotic, the antimicrobial may deactivate the probiotic. It is also desirable for the antimicrobial agent selected to be one that is non-leachable from the elastomeric film layers during the leaching step, so that the antimicrobial is not completely removed or washed out of the film during this leaching step. The antimicrobial agents tested herein, and many other examples described herein, are non-leachable in the leaching step.

Step (v-2) —Application of a Coating Composition

In one optional step, a coating composition may be applied to the elastomeric film on the former prior to the curing step. This coating application step will usually follow after the pre-leaching step described at (v-1) above. A coating composition may additionally, or alternatively, be applied following the curing step (vi) described below, or in an off-line process.

The coating composition applied at this time may comprise a coating polymer or polymer emulsion that provides slip properties to aid donning of the article (e.g. glove). The coating applied may be described as a polymer coat. A polymer coat may be applied whether or not chlorination is performed later. The concentration of polymer in the coating composition may be in the range of from about 0.1% to about 5% by weight of the coating composition, for example from about 0.5% to about 3% by weight of the coating composition. If chlorination is to be performed, then the concentration of polymer is typically at the lower end of the range (e.g. up to 1%). If there is to be no chlorination, then the concentration of polymer is typically at the higher end of the range (e.g. above 1%).

During this stage, the coating composition may be formulated to include a skin-protective agent, to provide both slip-properties and skin-protective properties on one surface (the inner surface) of the elastomeric article. Alternatively, a conventional polymer coat may be applied, and the skin-protective agent may be applied through another technique described herein. In these embodiments, the polymer coat may constitute the barrier layer (when present). Details of the application of a skin-protective agent in this polymer coating, after curing, including the composition of the coating, are described further below.

Step (vi) Curing the Layered Elastomeric Film on the Former

A curing step is performed prior to stripping of the articles from the former. This step usually involves curing conditions to cure the elastomeric film. The curing step is well known in the art, and suitable conditions for this step are as described in the PCT publications referred to above.

Step (vii) Post-Curing Steps

After curing but prior to stripping of the article from the former, additional steps can be performed. Such optional steps may include cooling (former cooling in water), chlorination, post-leaching, applying a coating material, and additional drying steps.

Step (vii-1) Chlorination

Optionally, the article may be subjected to chlorination after curing. This may follow former cooling in water. Chlorination is a process that changes the surface properties of the elastomeric article. For example, gloves subjected to chlorination have improved donning properties. The chlorination may be performed regardless of whether a polymer coat has been applied. The chlorination may be performed at a concentration range of 400-1000 ppm, for example about 600-1000 ppm. The chlorination may be performed at a lower concentration, for example 400-600 ppm, if there has been the application of a polymer coating. If there has been no application of a polymer coating prior to curing, then chlorination may be performed at a higher concentration, for example 600-1000 ppm.

Step (vii-2) Post-Leaching

Post-leaching may optionally be performed after curing. This may follow a chlorination step (if chlorination is performed).

Step (vii-3) Post-Cure Application of a Coating Composition

In some embodiments, the skin-protective agent is applied as a part of a coating composition after curing and prior to stripping of the article from the former. This coating composition may optionally contain a polymer coating material. Further details of this optional step are provided below. If the skin-protective agent is being applied through a different technique (e.g. if it is present in the latex composition of the last film layer applied, or if a coating is applied in an off-line process), then this step may be omitted.

Step (vii-4) Drying

The article, and if present, the coating on the article, may be dried in a final drying step prior to stripping. Drying may be conducted at a temperature above ambient and below 90° C.—for example, around 50-60° C.

Step (vii-5) Partial Stripping and Application of a Coating Composition

Optionally, the article maybe partially stripped from the former, and an antimicrobial agent applied as part of a coating composition onto the partially stripped surface in an on-line process. For example, in embodiments where the article is a glove, the glove may be partially stripped to the finger. A coating composition comprising the antimicrobial agent may then be applied to the partially stripped surface, for example by spray coating, and then allowed to dry (completely or partially).

Step (viii) Stripping

The film or article is fully stripped from the former at the conclusion of the formation process.

Step (ix) Post-Stripping Steps

After stripping, the glove may be subjected to post-stripping treatments, such as the application of a coating composition in an off-line process (e.g. a tumbling process).

This optional step is described in further detail below. If a coating composition is applied by tumbling at this stage, then it may not be necessary to applying a coating composition at one of the earlier stages.

The elastomeric articles, such as gloves, may be packaged to protect and/or preserve either or both of the antimicrobial agent and skin-protective agent on the surfaces thereof. The packaging may be in pairs, or the packaging may be of larger numbers of articles together. The packaging may be a sealed package that prevents contact with the external environment of the package. The package may be a vacuum pack.

Application of a Coating Composition Comprising a Skin-Protective Agent to Elastomeric Film The single-layer or multilayer film may be coated with a coating composition comprising the skin-protective agent (probiotic, prebiotic, or combination thereof).

There are a number of different techniques that may be employed to form a coating layer comprising the skin-protective agent on the film surface. Suitable techniques include online techniques such as dipping and spray-coating, and offline techniques such as tumbling.

In one example, a coating composition comprising the skin-protective agent is applied by a dipping process. This technique involves dipping of the elastomeric film on the former into a coating composition comprising the skin-protective agent. The coating composition may then be dried while the elastomeric article is on the former, followed by stripping of the article from the former. In the case of a dipping processes, or dip-coating, the step of applying coating composition comprising the skin-protective agent can be performed at any suitable time in the article manufacturing process, following formation of the elastomeric film layer(s) on the former. In one example, it is suitably applied after curing of the elastomeric film, but prior to stripping of the cured film from the former. In such cases, the coating can be applied after curing and chlorination. The coating may be applied after post-leaching. The articles may then be dried to dry the applied coating prior to stripping from the former. In another alternative, the step of applying the coating composition comprising the skin-protective agent can be performed following formation of the elastomeric film layer (after dipping, and after any pre-leaching of the wet gel film), prior to curing. In these embodiments, the coating composition is preferably free of heat-sensitive probiotics, which are generally not compatible with typical curing temperatures.

In another example, the coating composition comprising the skin-protective agent is applied by spray-coating. This technique involves spraying a coating composition comprising the skin-protective agent onto the elastomeric film on the former. The former may be rotated during spraying to ensure that the coating composition is applied evenly on each film or article. The coating composition may then be dried while the elastomeric article is on the former, and then the article is stripped form the former. In the case of spray-coating, the timing of the step is also suitably after curing of the elastomeric film of the elastomeric article. However, it is possible for the spray coating step to be performed after formation of the film, but prior to curing. The film in this case may be a dipped elastomeric film, or it may be an extruded elastomeric product. The coating composition comprising the skin-protective agent can in that case be spray-coated onto the extruded elastomeric article.

The coating composition comprising the skin-protective agent may alternatively be applied by tumbling, with or without spraying. This technique involves preparing the article by a dip coating method, an extrusion method or otherwise, stripping the article from the former (if prepared by dip coating), and then tumbling the article with the coating composition comprising the skin-protective agent in a tumbling process. The coating composition may be applied in a tumble dryer via a pump sprayer or through addition of the liquid coating composition into the dryer by another technique. In the case of spraying, spraying occurs while the articles are tumbled to ensure that the coating composition is applied evenly on each glove. The volume of coating composition applied may typically be in the range of about 1.5 mL or more per 500 $cm^2$ article. Drying in the tumble dryer results in evaporation of the solvent component of the coating composition, to leave the skin-protective agent (and any other non-volatile components) on the surface of the elastomeric article. Drying typically continues in the tumble dryer for a further time period of at least 5 minutes (e.g. 10 to 120 minutes, preferably 15 to 60 minutes), at a temperature above ambient temperature (e.g. more than 35° C., preferably 40 to 70° C.), after all of the coating composition has been applied. Preferably the skin-contacting surface of the articles are facing outwardly during the tumbling process to apply the coating to the exposed surface. The articles can be re-inverted thereafter.

The coating composition may comprise:
a skin-protective agent, and
a solvent, preferably water.

The coating composition preferably comprises:
a skin-protective agent,
optionally one or more of a dispersing agent, an emulsifier, a solubiliser, a rheology modifier, a wetting agent, an emollient, a skin conditioning agent, a humectant, a biocide, a preservative, silicone, fragrance and a pH adjustor; and
water.

If the skin-protective agent is to be applied as a part of a polymer coating composition, then the coating composition preferably comprises:
a skin-protective agent, preferably a thermally stable skin-protective agent, selected from a probiotic, a prebiotic or a combination thereof;
a coating polymer (described in further detail below);
optionally one or more of a dispersing agent, an emulsifier, a solubiliser, a rheology modifier, a wetting agent, an emollient, a skin conditioning agent, a humectant, a biocide, a preservative, silicone, fragrance and a pH adjustor; and
water.

The coating composition may contain the skin-protective agent in a total amount of at least about 0.0005% or at least about 0.001% by weight of the coating composition. The amount may be a minimum of 0.01%, 0.05%, 0.1%, 0.2%, 0.5%, 0.8%, 1.0% or 5% by weight of the coating composition. The amount may be a maximum of 50%, 40%, 35%, 30%, 25%, 20%, 18%, 15%, 12%, 10% or 8% by weight of the coating composition. Any minimum and maximum may be combined to form a range, such as between 0.5%-20% by weight of the coating composition.

In some optional embodiments, the coating composition may comprise a coating polymer, and may be described as a polymer coating composition. As described above, when the skin-protective agent is applied as a part of a polymer coating composition, this may be applied either prior to curing (see step (v-2)) or after curing (and after post-leaching; see step (vii-3)). When applied prior to curing, the coating composition is preferably free of heat-sensitive probiotics, which are generally not compatible with typical curing temperatures. When applied after curing, the temperature of any drying step prior to stripping needs to be set to ensure compatibility with any heat-sensitive probiotics present, or the skin-protective agents should be selected for compatibility with the drying conditions applied.

The formulation of the polymer coating composition may correspond to that known in the art for producing an inner coating on a glove for enhancing donning properties, with added skin-protective agent. Such coating compositions contain a coating polymer.

The coating polymer is a polymer that provides a coating on the surface of the elastomeric film. The coating polymer may be selected from polyacrylic emulsion, a polyurethane emulsion, a silicone emulsion, paraffin wax, polyethylene waxes, or a combination thereof. The amount of the coating polymer in the coating composition may be a minimum of 0.01%, and a maximum of 20% by weight of the polymer composition. The coating polymer preferably constitutes a maximum of 5% by weight of the coating composition, and where it is intended to apply a polymer coating and perform chlorination, preferably a maximum of 1% by weight of the coating composition. The minimum amount is preferably at least 0.1%, preferably 0.5% by weight of the coating composition. Any of the usual components in polymer coatings used in glove manufacture may be included in the coating composition, in typical amounts. These may include a dispersing agent, a rheology modifier, a wetting agent, a biocide and/or a pH adjustor. The balance is typically water. The rheology modifier may be present in an amount of 0-5% by weight (e.g. 0.01-2% by weight), the wetting agent may be present in amounts within the same range. The pH adjustor may be an agent for increasing or reducing the pH of the composition, and may be an acid or a base. The target pH of the coating composition should be between 4.0 and 8.0, preferably between 5.0 and 6.0. If pH conditions are outside of this range, there is a risk of degradation of beneficial skin flora. It is also necessary for the pH conditions to suit the conditions used for the manufacture of elastomeric film articles, where pH is also a factor.

If a polymer coating composition is applied, then chlorination may be omitted from the process. Alternatively, a polymer coating may be applied, and chlorination may be performed. In these embodiments, the concentration of polymer in the coating composition and the concentration of chlorine used are typically lower. For example, the concentration of polymer in the coating composition may be 0.5-3% by weight of the coating composition, and the concentration of chlorine may be 400-600 ppm.

The coating composition is preferably hydrogel free. The final coating is also preferably a non-gelled coating. The coating composition is preferably free of alginates, such as sodium alginate.

The coating composition is suitably dried on the glove surface to yield a dry surface. In some embodiments, the coating composition is dried to yield a dry, dehydrated surface. The coating is suitably a dry dehydrated coating.

In relation to post-curing application of a coating composition comprising a skin-protective agent, given that a heat-sensitive probiotic may be present, the coating and drying conditions should be suitably selected so as to maintain the stability of any heat-sensitive probiotic(s). The applicant has determined that the coating composition should be applied at a temperature below 50° C., preferably between 25° C. and 35° C. Whilst a temperature below 50° C. is the preference, it is permissible for the coating composition or the film containing the coating composition to be subjected to higher temperature conditions (e.g. up to 60° C.) for a short duration. The duration of higher temperature conditions (above 50° C. but preferably below 60° C.) should not be greater than 500 seconds or more preferably not greater than 200 seconds. Maintaining the temperature conditions to a temperature of not more than 50° C. during application of the coating composition is a feature of preferred embodiments of the invention. In some embodiments, the temperature is not raised above 60° C. during any stage of the coating process. In some embodiments, the temperature conditions may be not more than 48° C., not more than 46° C., not more than 44° C., not more than 42° C. or not more than 40° C.

After applying the coating composition, the coating may be dried in a final drying oven. The drying temperature may be above 60° C. to not more than 130° C., however in some embodiments, the drying temperature is contained to 40-60° C. to avoid degradation of any heat-sensitive probiotics present. In the case of low heat drying (i.e. drying at less than 60° C.), air blowers can be used to speed up the drying.

If the coating composition is applied prior to curing, given that curing is typically conducted in curing ovens at around 90° C. or more, the skin-protective agents should be selected from thermally stable skin-protective agents, such as thermophile probiotics and heat resistant prebiotics.

Application of a Coating Composition Comprising an Antimicrobial Agent to Elastomeric Film Whilst the antimicrobial agent is preferably incorporated into the elastomeric film article through incorporation into the coagulant or incorporation into the elastomeric film-forming composition used to produce one film layer of the product, another alternative is to incorporate the antimicrobial agent through coating of an elastomeric article with an antimicrobial-coating composition. This coating composition should be applied to the surface of the film that will be the external surface of the article.

The elastomeric article may be produced by a dipping process as described in detail above via steps (i) to (ix), with or without antimicrobial agent being incorporated into the coagulant or first dipped layer, or the elastomeric article may be produced by any other process such as extrusion. The elastomeric article may be manufactured by another supplier, and an antimicrobial-coating composition applied to that article (with the application of a coating composition comprising the skin-protective agent applied to the opposite surface).

The antimicrobial agent may be applied to the elastomeric article by any suitable technique, such as a tumbling method, with or without spraying. The antimicrobial agent may be applied in an on-line process or an off-line process.

In one example, in an off-line process, dried or partially dried elastomeric articles are stripped from the formers (step (viii) above) and placed in a tumble dryer. An antimicrobial-coating composition is prepared which comprises the antimicrobial agent. The coating composition typically comprises a solvent such as water to aid in application of the desired amount of the antimicrobial agent to the articles. The coating composition may be applied in a tumble dryer via a pump sprayer or through addition of the liquid coating composition into the dryer by another technique. In the case of spraying, spraying occurs while the articles are tumbled to ensure that the coating composition is applied evenly on each glove. The volume of coating composition applied may typically be in the range of about 0.01 L or more, such as about 0.01 L to about 100 L. Drying in the tumble dryer results in evaporation of the solvent component of the coating composition, to leave the antimicrobial agent (and any other non-volatile components) on the surface of the elastomeric article. Drying typically continues in the tumble dryer for a further time period of at least 5 minutes (e.g. 10 to 120 minutes, preferably 15 to 60 minutes), at a temperature above ambient temperature (e.g. more than 35° C., preferably 40 to 70° C.), after all of the coating composition has been applied. It is ensured that the external surface (i.e. the non-skin-contacting surface) of the articles are facing outwardly during the tumbling process to apply the coating comprising the antimicrobial agent to the exposed surface. In the case of articles comprising a skin-protective agent on the internal surface (i.e. the skin-contacting surface) of the article, slow tumbling (i.e. tumbling at a rotational frequency of not more than 60 revolutions per minute) may be used to reduce the likelihood of the antimicrobial agent entering the internal surface of the article.

In another example, in an on-line process, dried or partially dried elastomeric articles are partially stripped from the formers and spray coated with an antimicrobial-coating composition on the partially stripped surface of the articles. The antimicrobial coating is then allowed to dry (completely or partially) before the article is fully stripped from the former.

The coating composition may contain the antimicrobial agent in an amount of at least about 0.0005% or at least about 0.001% by weight of the coating composition (i.e. total amount in the case of a combination of antimicrobial agents). The amount may be a minimum of 0.01%, 0.05%, 0.1%, 0.2%, 0.5%, 0.8% or 1.0% by weight of the coating composition. The amount may be a maximum of 50%, 40%, 35%, 30%, 25%, 20%, 18%, 15%, 12%, 10%, 8% or 5% by weight of the coating composition. Any minimum and maximum may be combined to form a range, such as between 0.5%-20% or 0.5-10% by weight of the coating composition.

Illustration of Options for Production of the Articles

In the first table below, a number of options described above for production of the articles are outlined, to aid understanding of possible sequences of steps. Some options include off-line steps. The options outlined in methods 1 and 2, which are commercially practical and cost-effective options, are preferred. In the table, the article is a glove and includes a barrier layer containing no anti-microbial or skin-protective agent. The barrier layer may be a barrier film layer, which may contain a filler, or a coating layer.

| Steps (in order) | Method 1 | 2 | 3 | 4 | 5 | 6(i) | 6(ii) |
|---|---|---|---|---|---|---|---|
| Washing of Former | ✓ | ✓ | ✓ | ✓ | ✓ | ✓ | ✓ |
| Coagulant dip | ✓ | ✓ | ✓ | ✓ with AM | ✓ with or without AM[f] | ✓ with or without AM[f] | ✓ |
| Coagulant drying | ✓ | ✓ | ✓ | ✓ | ✓ | ✓ | ✓ |
| Latex dip 1 | ✓ With AM | ✓ With AM | ✓ with AM | ✓ option to add AM | ✓ with or without AM[f,g] | ✓ with or without AM[f,g] | ✓ |
| Latex gel film dried or partially dried | ✓ | ✓ | ✓ | ✓ | ✓ | ✓ | ✓ |
| Latex dip 2 | ✓ | ✓ | ✓ | Optional[b] | Optional[b] | Optional[b] | Optional[b] |
| Latex gel film dried or partially dried | ✓ | ✓ | ✓ | Optional | Optional | Optional | Optional |
| (Optionally repeat latex dipping/drying steps for more layers) | Optional | Optional | Optional | Optional | Optional | Optional | Optional |
| Final latex dip containing SPA | x | x | x | x | ✓ | x | x |
| Latex gel film dried or partially dried | x | x | x | x | ✓ | x | x |
| Pre-leaching | ✓ | ✓ | ✓ | ✓ | ✓ | ✓ | ✓ |
| Polymer coating (Polymer Bath) | ✓ optionally with SPA[a] | x | ✓ optionally with SPA[a] | Optional[c] | Optional[c] | Optional[c] | Optional[c] |
| Curing | ✓ | ✓ | ✓ | ✓ | ✓ | ✓ | ✓ |
| Former cooling in water | ✓ | ✓ | x | ✓[d] | ✓[d] | ✓[d] | ✓[d] |
| Chlorination | ✓ | ✓ | x | Optional[e] | Optional[e] | Optional[e] | Optional[e] |
| Post-leaching | ✓ | ✓ | ✓ | ✓ | ✓ | ✓ | ✓ |
| Skin-protective agent coating (Slurry Tank) | ✓ | ✓ | ✓ | ✓ | ✓ | x | ✓ |
| Drying | ✓ | ✓ | ✓ | ✓ | ✓ | ✓ | ✓ |
| Glove striped until to finger | ✓ | ✓ | ✓ | ✓ | ✓ | ✓ | ✓ |
| AM Spraying | Optional | Optional | Optional | Optional | Optional | Optional | Optional |
| Drying of AM | Optional | Optional | Optional | Optional | Optional | Optional | Optional |
| Glove fully stripped | ✓ | ✓ | ✓ | ✓ | ✓ | ✓ | ✓ |
| Invert gloves | x | x | x | x | x | ✓ | x |
| Place gloves inside tumbler | x | x | x | x | x | ✓ | ✓ |

| Steps | Method | | | | | | |
|---|---|---|---|---|---|---|---|
| (in order) | 1 | 2 | 3 | 4 | 5 | 6(i) | 6(ii) |
| Spraying of coating | x | x | x | x | x | ✓, contains SPA | ✓, contains AM |
| Drying of coating in tumbler | x | x | x | x | x | ✓ | ✓ |
| Turn gloves inside-out | x | x | x | x | x | ✓ | x |

Key: AM = antimicrobial; SPA = skin-protective agent

Table Notes:

a. If skin-protective agent is added, it is a heat-resistant skin-protective agent. If skin-protective agent is not added, then the polymer coating may form a barrier coating layer.

b. If antimicrobial is in the first latex dip, then this step may be performed to form a barrier film layer.

c. If a polymer coating is applied, it may be applied together with or without chlorination. The polymer coating may contain a heat-resistant skin-protective agent.

d. Cooling can be omitted if no chlorination follows this step.

e. If no polymer coating is applied, then chlorination is performed. If a polymer coating is applied, it may be applied together with or without chlorination being performed.

f. Antimicrobial is included in at least one of the coagulant or the first latex dip composition, and may be included in both.

g. If there is no antimicrobial in the latex composition, then this latex layer may form a barrier film layer.

FIG. 1 illustrates elastomeric articles containing a barrier layer that can be prepared by the methods described in the first table above. In particular, FIG. 1 shows possible arrangements of the coatings and layers, and possible locations of the anti-microbial agent, skin-protective agent and barrier layer in those coatings and layers, based on the sequence of steps performed. It is noted that the layer denoted A1 is a coagulant layer. While this is depicted as a distinct "layer", it is to be understood that the coagulant layer does not remain as a distinct layer or coating in the final article, but rather is incorporated into (or merges into) the first layer of film formed during production of the elastomeric film. Accordingly, antimicrobial agent present in the first elastomeric film layer will be present on the outer layer of the final elastomeric article. It is also noted that the layer denoted C may include a layer of polymer coating, a layer of donning coating, or both. While not depicted in the embodiments shown in FIG. 1, the layer of polymer coating may optionally be a barrier layer.

The second table below outlines a number of options for production of articles, in particular gloves, that do not include a barrier layer. The options outlined in methods A and B, which are commercially practical and cost-effective options, are preferred.

| Steps | Method | | | | | | |
|---|---|---|---|---|---|---|---|
| (in order) | A | B | C | D | E | F(i) | F(ii) |
| Washing of Former | ✓ | ✓ | ✓ | ✓ | ✓ | ✓ | ✓ |
| Coagulant dip | ✓ | ✓ | ✓ | ✓ with AM | ✓ with or without AM[5] | ✓ with or without AM[5] | ✓ |
| Coagulant drying | ✓ | ✓ | ✓ | ✓ | ✓ | ✓ | ✓ |
| Latex dip 1 | ✓ With AM | ✓ With AM | ✓ with AM | ✓ with SPA | ✓ with AM | ✓ with or without AM[5,] | ✓ with SPA |
| Latex gel film dried or partially dried | ✓ | ✓ | ✓ | ✓ | ✓ | ✓ | ✓ |
| (Optionally repeat latex dipping/drying steps for more layers) | ✓ with AM | ✓ with AM | ✓ with AM | ✓ with SPA | ✓ with either AM or SPA | ✓ with either AM or SPA | ✓ with SPA |
| Final latex dip containing SPA | x | x | x | x | ✓ | x | x |
| Latex gel film dried or partially dried | x | x | x | x | ✓ | x | x |
| Pre-leaching | ✓ | ✓ | ✓ | ✓ | ✓ | ✓ | ✓ |
| Polymer coating (Polymer Bath) | Optional[1] | x | Optional[1] | Optional[1,2] | Optional[1,2] | Optional[1,2] | Optional[1,2] |
| Curing | ✓ | ✓ | ✓ | ✓ | ✓ | ✓ | ✓ |
| Former cooling in water | ✓ | ✓ | x | ✓[3] | ✓[3] | ✓[3] | ✓[3] |

-continued

| Steps (in order) | A | B | C | D | E | F(i) | F(ii) |
|---|---|---|---|---|---|---|---|
| Chlorination | ✓ | ✓ | x | Optional[4] | Optional[4] | Optional[4] | Optional[4] |
| Post-leaching | ✓ | ✓ | ✓ | ✓ | ✓ | ✓ | ✓ |
| Skin-protective agent coating (Slurry Tank) | ✓ | ✓ | ✓ | ✓ | ✓ | x | ✓ |
| Drying | ✓ | ✓ | ✓ | ✓ | ✓ | ✓ | ✓ |
| Glove striped until to finger | ✓ | ✓ | ✓ | ✓ | ✓ | ✓ | ✓ |
| AM Spraying | Optional | Optional | Optional | Optional | Optional | Optional | Optional |
| Drying of AM | Optional | Optional | Optional | Optional | Optional | Optional | Optional |
| Glove fully stripped | ✓ | ✓ | ✓ | ✓ | ✓ | ✓ | ✓ |
| Invert gloves | x | x | x | x | x | ✓ | x |
| Place gloves inside tumbler | x | x | x | x | x | ✓ | ✓ |
| Spraying of coating | x | x | x | x | x | ✓, contains SPA | ✓, contains AM |
| Drying of coating in tumbler | x | x | x | x | x | ✓ | ✓ |
| Turn gloves inside-out | x | x | x | x | x | ✓ | x |

Key: AM = antimicrobial; SPA = skin-protective agent

Table Notes:
1. If a polymer coating is applied, heat-resistant skin-protective agent is added.
2. If a polymer coating is applied, it may be applied together with chlorination or without chlorination. The polymer coating may contain a heat resistant skin-protective agent.
3. Cooling can be omitted if no chlorination follows this step. Cooling is required if chlorination is performed.
4. If no polymer coating is applied, then chlorination is performed. If a polymer coating is applied, it may be applied together with or without chlorination being performed.
5. Antimicrobial is included in at least one of the coagulant or the first latex dip composition, and may be included in both.

FIG. 2 illustrates elastomeric articles without a barrier layer that can be prepared by the methods described in the second table above. In particular, FIG. 2 shows possible arrangements of the coatings and layers, and possible locations of the anti-microbial agent and skin-protective agent in those coatings and layers, based on the sequence of steps performed.

Figure 3:
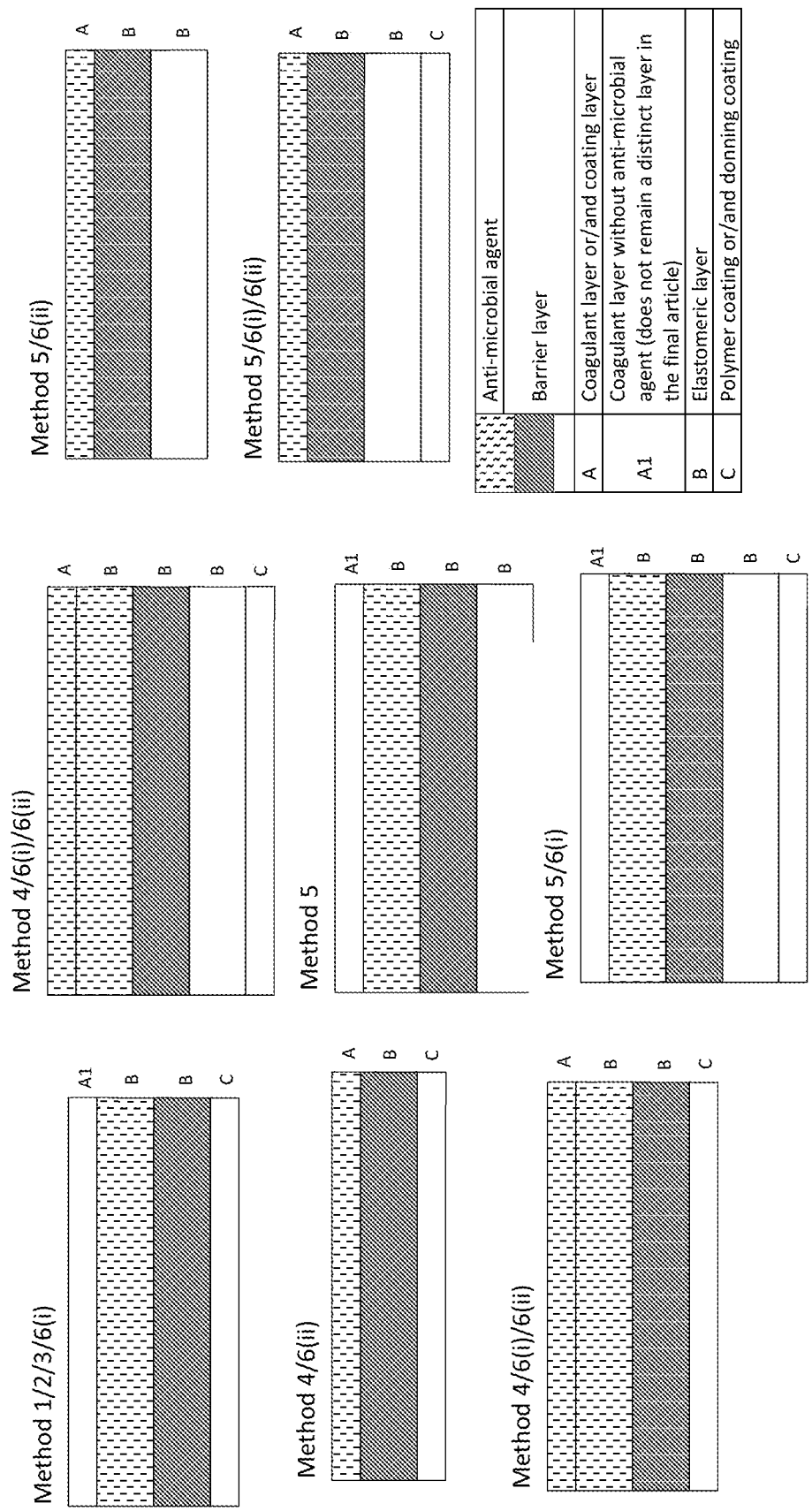
FIG. 3 is a schematic illustration of other forms of elastomeric articles based on an antimicrobial agent and a barrier layer.

FIG. 3 illustrates elastomeric articles containing a barrier layer and an antimicrobial agent on the external surface of the article (without any skin-protective agent on the internal surface).

Figure 4:
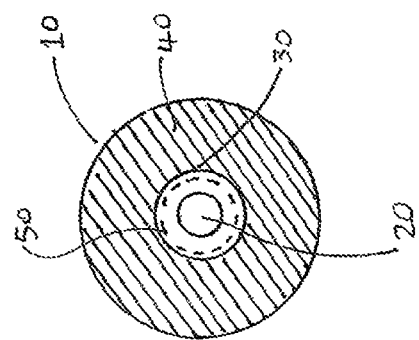
FIG. 4 is an indicative illustration of a plate demonstrating the test results for a sample taken from a glove, demonstrating that the tested surface of the sample has an antimicrobially-effective amount of an antimicrobial agent.

FIG. 4 illustrates a plate (10) that has been prepared following the test procedure for determining whether a surface of a film is "free of an antimicrobially effective amount of an antimicrobial agent". In FIG. 4, the 1.6 cm-sized diameter disc of the test film (20) is illustrated, placed centrally on the plate (10) coated with the bacterium of interest. Growth of the bacterium of interest is inhibited within a zone that extends between the edge of the disc (20) and the margin (30) of the bacterial growth zone, shown as a shaded area (40). A dashed line (50) shown in FIG. 4 represents a 4 mm zone of inhibition distance. In FIG. 4, the distance zone of inhibition (between (20) and (30)) is greater than 4 mm, indicating that an antimicrobially-effective amount of the antimicrobial agent is present on the test film disc (20).

Definitions

As used in the specification and the appended claims, the singular forms "a," "an" and "the" include plural referents unless the context clearly dictates otherwise. Thus, for example, reference to "an antimicrobial agent" includes one, two or more antimicrobial agents.

In the claims and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

EXAMPLES

The invention will now be described in further detail with reference to the following non-limiting examples produced in accordance with embodiments of the invention.

Testing of Glove Properties

Glove are tested to determine the following properties:
Bactericidal efficacy (% bacterial reduction)
Modulus at 300%
Modulus at 500%
Tensile strength (MPa/Psi) (1 MPa=145 Psi)
Elongation %; and
Force at break (N).

Bactericidal efficacy can be measured in accordance with the procedure specified in ASTM D7907 (Method A, Standard Test Methods for Determination of Bactericidal Efficacy on the Surface of Medical Examination Gloves). The standard is readily available. The test can be applied to multilayer films and elastomeric articles including gloves (such as examination gloves for medical applications).

Tensile strength, stress at 300% and 500% modulus and elongation to break are measured by testing procedures conducted in accordance with ASTM D 412-16, based on the sample size set by the standard for gloves. The gloves are also tested for force at break measured in accordance with EN 455. The standards are readily available. These tests can be applied to multilayer films and gloves (such as examination gloves for medical applications). Tensile strength, modulus at 300% and modulus at 500% are each measured in units of MPa, and the elongation (or elongation at break) in %.

Multilayer Glove Products Containing an Antimicrobial Agent in the External Layer Example 1: Antimicrobial Agent within Elastomeric Film-Forming Composition Gloves were prepared from the compositions set out below in Table 1 using standard elastomeric film production processes as known in the art.

TABLE 1

Elastomeric film-forming compositions used to form first (external) latex layer and second (internal) latex layer

| | Dosage (phr) | |
|---|---|---|
| Ingredients | First latex layer | Second latex layer |
| Carboxylated acrylonitrile latex | 100 | 100 |
| Potassium hydroxide | 1.5 | 1.5 |
| Stabiliser | 0.1 | 0.1 |
| Sulfur | 0.15 | 0.15 |
| Accelerator | 0.05 | 0.05 |
| Zinc Oxide | 0.3 | 0.3 |
| Antioxidant | 0.2 | 0.2 |
| Titanium Dioxide | 2.0 | 2.0 |
| Zinc pyrithione | 1.0 to 4.0 | 0 |
| Antifoam | 0.06 | 0.06 |
| Pigment | As per requirement | As per requirement |

The stages of glove production included:
1. Dipping a glove-shaped former into a coagulant, containing 13% calcium nitrate, 1.5% metallic stearate (potassium and/or calcium stearate), 0.1% wetting agent (non-ionic alcohol ethoxylate) and no antimicrobial or skin-protective agents, followed by drying.
2. Dipping the former into the first latex layer composition, followed by partial drying of that layer to the gel state. Samples were produced containing differing amounts of the zinc pyrithione, including a control (0 phr), and sets 1 (1 phr), 2 (2 phr), 3 (3 phr) and 4 (4 phr).
3. Dipping the former into the second latex layer composition, followed by partial drying of that layer to the gel state.
4. Leaching (pre-leaching), involving dipping into an aqueous leaching liquid.
5. Curing of the elastomeric film in an oven at a temperature of 100 to 120° C. for 20 minutes.
6. Cooling of the former and film by dipping into room temperature water.
7. Chlorination, with a chlorine concentration of 600-800 ppm.
8. Glove rinsing/post-leaching.
9. Application of a coating composition having the formulation set out in Table 2 below, by a dipping method, to produce a coating on the donning surface of the gloves.
10. Drying in an oven at a temperature of 50° C.-60° C. for 5 minutes, followed by stripping of the gloves from the former.

TABLE 2

Prebiotic and probiotic coating composition

| Ingredients | Percentage of composition (%) |
|---|---|
| Beta-glucan | 0.02 |
| Inulin | 0.5 |
| Alpha-glucan | 0.5 |
| *Lactobacillus brevis* extract | 2 |
| Emulsifiers | 5 |
| Rheology modifier | 0.5 |
| Wetting agent | 0.1 |
| Water | 91.38 |

The finished gloves had a thickness (measured at the palm) of 0.08 mm±0.02 mm. The unaged and aged physical properties of the gloves were tested using ASTM D412 and EN455 methods, and the results are tabulated in Tables 3 and 4, respectively. The aging results relate to accelerated aging at 100° C. for 22 hours.

TABLE 3

Physical properties of unaged gloves

| Set | Zinc pyrithione dosage (phr) | Tensile Strength (MPa) | Modulus at 500% (MPa) | Elongation at break (%) | Force at break (N) |
|---|---|---|---|---|---|
| Control | 0 | 18.52 | 3.47 | 786 | 8.61 |
| 1 | 1.0 | 16.17 | 3.61 | 761 | 6.15 |
| 2 | 2.0 | 17.39 | 3.60 | 774 | 7.04 |
| 3 | 3.0 | 18.45 | 4.41 | 746 | 7.77 |
| 4 | 4.0 | 21.29 | 4.87 | 741 | 8.56 |

TABLE 4

Physical properties of gloves samples after accelerated aging

| Set | Zinc pyrithione dosage (phr) | Tensile Strength (MPa) | Modulus at 500% (MPa) | Elongation at break (%) | Force at break (N) |
|---|---|---|---|---|---|
| Control | 0 | 17.67 | 3.55 | 783 | 7.42 |
| 1 | 1.0 | 14.94 | 4.07 | 727 | 6.98 |
| 2 | 2.0 | 14.46 | 4.51 | 688 | 8.28 |
| 3 | 3.0 | 15.59 | 4.68 | 698 | 7.93 |
| 4 | 4.0 | 18.98 | 4.50 | 741 | 8.96 |

All gloves passed the standard requirements of ASTM D6319 and EN 455. These results indicate that the physical properties of the gloves prepared using zinc pyrithione in the elastomer composition are as good as, or better, than the control glove as indicated. The range of tensile strength values for the products were within the range of 10 to 25 MPa, the modulus values at 500% were within the range of 3 to 8 MPa; the elongation at break values were within the range of 700 to 900% and the force at break values were within the range of 6N to 10 N, for both the control product and the exemplified products of the invention.

The gloves of set 3 containing 3.0 phr zinc pyrithione were also tested for their bactericidal activity, as compared to the control glove. The results are shown in Table 5, which shows the percentage of bacterial reduction of the glove prepared using 3.0 phr zinc pyrithione in the outer latex layer (set 3) compared with control glove. The percentage was measured by reduction of pathogenic bacteria count following contact with the bacterial cultures at 5, 10, 20 and 30 minutes post-exposure. The results indicate that the presence of the antimicrobial agent zinc pyrithione in the outer layer of the glove provides the glove with effective antimicrobial activity.

TABLE 5

Bactericidal efficacy of gloves based on time-kill study

| | Percentage of Bacterial Reduction (%) | | | |
|---|---|---|---|---|
| Time (min) | 5 | 10 | 20 | 30 |
| Enterococcus faecalis | 99.99 | 99.99 | 99.99 | 99.99 |
| Klebsiella pneumoniae | 99.99 | 99.99 | 99.99 | 99.99 |
| Staphylococcus aureus | 99.99 | 99.99 | 99.99 | 99.99 |
| Pseudomonas aeruginosa | 99.78 | 99.99 | 99.99 | 99.99 |

Example 2: Antimicrobial Agent Incorporated into Coagulant

Gloves of a thickness of 0.08 mm+/−0.02 mm were prepared using the same procedure and components as outlined in Example 1 (steps 1 to 8), with the following changes:

The coagulant composition also contained 2-phenylphenol in an amount of 3% by weight—the coagulant formulation having the composition set out in Table 6 below. The control glove did not contain any 2-phenylphenol in the coagulant composition (i.e. Table 6 composition, with 2-phenylphenol removed, and the balance made up of water).

The first latex layer contained no 2-phenylphenol, in both the glove of Example 2 and the control.

TABLE 6

Coagulant composition containing 2-phenylphenol

| Ingredients | Percentage of composition (%) |
|---|---|
| Powder-free coagulant - metallic stearate (potassium and/or calcium stearate) | 1.5 |
| Wetting agent - alcohol ethoxylates (non-ionic surfactant) | 0.1 |
| Calcium nitrate | 13 |
| 2-Phenylphenol | 3 |
| Water | 82.4 |

As for the gloves in Example 1, the gloves of Example 2 (including the control) contained the coating composition set out in Table 2 on the internal (donning) surface.

The finished gloves were tested for their bactericidal activity. The results are shown in Table 7, which shows the percentage of bacterial reduction of the antimicrobial glove containing 2-phenylphenol in the outer latex layer compared with the control glove. The percentage was measured by reduction of pathogenic bacteria count following contact with the bacterial cultures at 5, 10, 20 and 30 minutes post-exposure. The results indicate that the presence of 2-phenylphenol antimicrobial agent in the coagulant composition used in the production of the glove provides the glove with effective antimicrobial activity compared to a control glove without antimicrobial agent.

TABLE 7

Bactericidal efficacy of gloves based on time-kill study.

| | Percentage of Bacterial Reduction (%) | | | |
|---|---|---|---|---|
| Time (min) | 5 | 10 | 20 | 30 |
| Enterococcus faecalis | 99.99 | 99.99 | 99.99 | 99.99 |
| Klebsiella pneumoniae | 99.99 | 99.99 | 99.99 | 99.99 |
| Staphylococcus aureus | 99.99 | 99.99 | 99.99 | 99.99 |
| Pseudomonas aeruginosa | 99.78 | 99.99 | 99.99 | 99.99 |

Single-Layer Glove Products

Example 3: Single-Layer Glove with a Coating on the Internal Surface

This example was conducted to test the efficacy of the skin protective coating at donning side of a test glove, in terms of preserving the skin microbiota, in comparison to the efficacy of the antibacterial agent on a surface of another test glove. It was postulated that the glove with antimicrobial agent would have germ killing effect, and that the glove with the skin-protective coating would not, and the example sought to establish whether this was in fact the case in a glove environment. Once established, this provides a baseline for assessing whether the addition of the antibacterial agent to the opposite side of the glove compared to the skin-protective agent adversely impacts on the skin-protective nature of that skin-protective surface of the glove.

Two variants of a single-layer glove were prepared using the following steps:
1. Dipping a glove-shaped former into a coagulant, containing 13% calcium nitrate, 1.5% powder-free coagulant (metallic stearate-potassium and/or calcium stearate), 0.1% wetting agent and no antimicrobial or skin-protective agents, followed by drying.
2. Dipping the former into the "second latex layer" composition set out in Table 1, to produce a single-layer of film on the former, followed by partial drying of that layer to the gel state.
3. Leaching (pre-leaching), involving dipping into an aqueous leaching liquid.
4. Curing the elastomeric film in an oven at a temperature of 100 to 120° C. for 20 minutes.
5. Cooling the former and film by dipping into room temperature water.
6. Performing chlorination (600-800 ppm chlorine concentration).
7. Applying the coating composition set out in Table 8 by dipping to produce the gloves of Set 1 and Set 2, respectively, having the coating on the donning surface.

TABLE 8

Example 3 coating compositions

| Ingredients | Set 1 Amount (wt %) | Set 2 Amount (wt %) |
|---|---|---|
| Beta-glucan | 0.02 | — |
| Inulin | 0.5 | — |
| Alpha-glucan | 0.5 | — |
| Lactobacillus brevis extract | 2 | — |
| 2-phenylphenol | | 3 |
| Emulsifiers | 5 | 5 |
| Rheology modifier | 0.5 | 0.5 |

TABLE 8-continued

Example 3 coating compositions

| Ingredients | Set 1 Amount (wt %) | Set 2 Amount (wt %) |
|---|---|---|
| Wetting agent | 0.1 | 0.1 |
| Water | 91.38 | 91.4 |

8. Drying in a drying oven at a temperature of about 50° C.-60° C. for 5 minutes, followed by stripping of the gloves from the former.

The finished gloves were tested for their bactericidal activity. The test was conducted by mixing a glove specimen with microorganism strains in a reference culture medium. Following 24 hours of incubation time, quantity of residual substrate was determined. The results are shown in Table 9. The results indicate that the probiotic and prebiotic coating selectively increased the growth of beneficial microbiota as indicated. The results also indicate that the antimicrobial coating indiscriminately killed both beneficial and undesirable microbiota as indicated.

TABLE 9

Microbiological activity of gloves having a coating with prebiotic and probiotic or a coating with an antimicrobial agent

| | Growth of strains | |
|---|---|---|
| Microbial Strains | Set 1 (Coating with prebiotic and probiotic) | Set 2 (Coating with antimicrobial agent) |
| Beneficial microbiota | | |
| Lactobacillus pentosus | Increased | Killed |
| Micrococcus kristinae | Increased | Killed |
| Corynebacterium xerosis | Increased | Killed |
| Staphylococcus capitis | Increased | Killed |

TABLE 9-continued

Microbiological activity of gloves having a coating with prebiotic and probiotic or a coating with an antimicrobial agent

| | Growth of strains | |
|---|---|---|
| Microbial Strains | Set 1 (Coating with prebiotic and probiotic) | Set 2 (Coating with antimicrobial agent) |
| Undesirable microbiota | | |
| Staphylococcus aureus | No growth | Killed |
| Propionibacterium acnes | No growth | Killed |

Example 4: Performance of Different Prebiotic and Probiotic Coating

Gloves containing antimicrobial agents were produced with the latex composition in Table 10 below.

TABLE 10

Latex composition of antimicrobial gloves.

| | Dosage (phr) | |
|---|---|---|
| Ingredients | First latex layer | Second latex layer |
| Carboxylated acrylonitrile latex | 100 | 100 |
| Potassium hydroxide | 1.5 | 1.5 |
| Stabiliser | 0.1 | 0.1 |
| Sulfur | 0.15 | 0.15 |
| Accelerator | 0.05 | 0.05 |
| Zinc Oxide | 0.5 | 0.3 |
| Antioxidant | 0.2 | 0.2 |
| Titanium Dioxide | 2.0 | 2.0 |
| Zinc pyrithione | 1.5 | 0 |
| Antifoam | 0.06 | 0.06 |
| Pigment | As per requirement | As per requirement |

The gloves were produced according to the methods described in Example 1. Prebiotic and probiotic coatings were applied to the donning surface of the gloves after curing and post-leaching steps, the compositions are described in Table 11.

TABLE 11

Composition of prebiotic and probiotic coating.

| | Percentage of composition (%) | | | | | | | | | | |
|---|---|---|---|---|---|---|---|---|---|---|---|
| Ingredients | Set 1&2 | Set 3&4 | Set 5&6 | Set 7&8 | Set 9&10 | Set 11&12 | Set 13&14 | Set 15&16 | Set 17&18 | Set 19&20 | Control |
| Inulin | 1&5 | 0 | 0 | 0 | 0 | 0 | 0 | 0 | 0 | 0 | 0 |
| Beta-glucan | 0 | 0.05& 0.1 | 0 | 0 | 0 | 0 | 0 | 0 | 0 | 0 | 0 |
| Alpha-glucan | 0 | 0 | 1&5 | 0 | 0 | 0 | 0 | 0 | 0 | 0 | 0 |
| Mixture of xylitol & lactitol (Brand: Ecodermine ™) | 0 | 0 | 0 | 2&4 | 0 | 0 | 0 | 0 | 0 | 0 | 0 |
| Leuconostoc (radish root) ferment | 0 | 0 | 0 | 0 | 2&4 | 0 | 0 | 0 | 0 | 0 | 0 |
| Lactobacillus ferment lysate | 0 | 0 | 0 | 0 | 0 | 2&4 | 0 | 0 | 0 | 0 | 0 |
| Thermus thermophiles ferment | 0 | 0 | 0 | 0 | 0 | 0 | 2&4 | 0 | 0 | 0 | 0 |
| Mixture of Lactobacillus ferment, GOS & FOS (Brand: Ecoskin ®) | 0 | 0 | 0 | 0 | 0 | 0 | 0 | 1&3 | 0 | 0 | 0 |

TABLE 11-continued

Composition of prebiotic and probiotic coating.

| | Percentage of composition (%) | | | | | | | | | | |
|---|---|---|---|---|---|---|---|---|---|---|---|
| Ingredients | Set 1&2 | Set 3&4 | Set 5&6 | Set 7&8 | Set 9&10 | Set 11&12 | Set 13&14 | Set 15&16 | Set 17&18 | Set 19&20 | Control |
| Mixture of sodium benzyl (0.5%), benzyl acid (2%), potassium sorbate (0.3%), sodium malic (2%) and aloe powder extract (1%). | 0 | 0 | 0 | 0 | 0 | 0 | 0 | 0 | 2&4 | 0 | 0 |
| Aloe powder extract | 0 | 0 | 0 | 0 | 0 | 0 | 0 | 0 | 0 | 5&10 | 0 |
| Emulsifiers | | | | | | | 5 | | | | |
| Rheology modifier | | | | | | | 0.5 | | | | |
| Wetting agent | | | | | | | 0.1 | | | | |
| Water | | | | | | | Add up to 100% | | | | |

*Remark: GOS is α-glucooligosaccharides, FOS is β-fructooligosaccharides. Both GOS and FOS are prebiotics.

Efficacy of the prebiotic and probiotic coating was tested according to the method described below:
1. *Lactobacillus casei* strain was used to evaluate efficacy of the prebiotic and probiotic coating.
2. Firstly, De Man, Rogosa and Sharpe (MRS) agar plate was prepared using MRS agar powder.
3. A 100 μL of *Lactobacillus casei* strain dissolved in peptone water was spread on the MRS agar.
4. A 50 μL of 0.05% phenoxyethanol (mild antimicrobial agent) was dropped at the center of agar plate. This is to simulate skin microbiota damaged by antimicrobial agent.
5. Glove specimen containing prebiotic and probiotic coating was cut into 1.6 cm diameter and was placed on top of the mild antimicrobial agent droplet. The surface coated with prebiotic and probiotic contacted with the agar plate. This is to simulate skin contact with the prebiotic and probiotic coating.
6. The plates were incubated at 36° C. for 48 hours.
7. Size of zone inhibition was measured following incubation. The zone inhibition was measured from the edge of the glove specimen to the edge of the zone inhibition. Measurements were conducted at three different areas and average of three readings was recorded.
8. The size of zone inhibition indicates efficacy of the coating in promoting growth of *Lactobacillus casei* cultured on agar plate. The lesser the zone inhibition, the higher the efficiency of the prebiotic and probiotic coating.
9. The results are illustrated in Table 12 below.

TABLE 12

Size of zone inhibition of gloves containing various prebiotic and probiotic coatings.

| Set | Size of zone inhibition (mm) |
|---|---|
| 1 | 5 |
| 2 | 3 |
| 3 | 6 |
| 4 | 2 |
| 5 | 4 |
| 6 | 3 |
| 7 | 3 |
| 8 | 2 |
| 9 | 5 |
| 10 | 3 |
| 11 | 6 |
| 12 | 2 |
| 13 | 4 |
| 14 | 3 |
| 15 | 5 |
| 16 | 4 |
| 17 | 7 |
| 18 | 8 |
| 19 | 7 |
| 20 | 8 |
| Control | 6 |

Set 4, 8 and 12 (each has 2 mm of inhibition zone) demonstrated good recovery of *Lactobacillus casei* culture as the size of zone inhibition was smaller than the control (6 mm). The prebiotic and probiotic coating in Set 4, 8 and 12 promoted growth of *Lactobacillus casei*. However, Set 17, Set 18 and Set 20 have demonstrated antimicrobial effect.

Example 5: Performance of Different Antimicrobial Agent

Gloves containing different antimicrobial agents in the first latex layer were produced in accordance with Table 13. The second latex layer was dipped according to the composition described in Table 10.

TABLE 13

Latex composition of first latex layer.

| Ingredients | Dosage (phr) | | | | | | | | | | |
|---|---|---|---|---|---|---|---|---|---|---|---|
| | Control | Set 1&2 | Set 3&4 &5 | Set 6&7 | Set 8&9 | Set 10&11 | Set 12&13 | Set 14&15 | Set 16&17 | Set 18&19 | Set 20&21 |
| Carboxylated acrylonitrile latex | 100 | 100 | 100 | 100 | 100 | 100 | 100 | 100 | 100 | 100 | 100 |
| Potassium hydroxide | 1.5 | 1.5 | 1.5 | 1.5 | 1.5 | 1.5 | 1.5 | 1.5 | 1.5 | 1.5 | 1.5 |
| Stabiliser | 0.1 | 0.1 | 0.1 | 0.1 | 0.1 | 0.1 | 0.1 | 0.1 | 0.1 | 0.1 | 0.1 |
| Sulfur | 0.15 | 0.15 | 0.15 | 0.15 | 0.15 | 0.15 | 0.15 | 0.15 | 0.15 | 0.15 | 0.15 |
| Accelerator | 0.05 | 0.05 | 0.05 | 0.05 | 0.05 | 0.05 | 0.05 | 0.05 | 0.05 | 0.05 | 0.05 |
| Zinc Oxide | 0.5 | 0.5 | 0.5 | 0.5 | 0.5 | 0.5 | 0.5 | 0.5 | 0.5 | 0.5 | 0.5 |
| Antioxidant | 0.2 | 0.2 | 0.2 | 0.2 | 0.2 | 0.2 | 0.2 | 0.2 | 0.2 | 0.2 | 0.2 |
| Titanium Dioxide | 2.0 | 2.0 | 2.0 | 2.0 | 2.0 | 2.0 | 2.0 | 2.0 | 2.0 | 2.0 | 2.0 |
| Antifoam | 0.06 | 0.06 | 0.06 | 0.06 | 0.06 | 0.06 | 0.06 | 0.06 | 0.06 | 0.06 | 0.06 |
| Pigment | | | | | As per requirement | | | | | | |
| Zinc pyrithione | 0 | 1& 1.5 | 0 | 0 | 0 | 0 | 0 | 1 | 1 | 1 | 1 |
| O-phenylphenol | 0 | 0 | 0.25& 0.5&1 | 0 | 0 | 0 | 0 | 0.25&0.5 | 0 | 0 | 0 |
| Piroctone olamine | 0 | 0 | 0 | 0.05& 0.1 | 0 | 0 | 0 | 0 | 0 | 0 | 0 |
| Phenoxy-ethanol | 0 | 0 | 0 | 0 | 0.5&1 | 0 | 0 | 0 | 0 | 0.5&1 | 0 |
| Mixture of phenoxyethanol, Caprylyl Glycol & Chlorphenesin | 0 | 0 | 0 | 0 | 0 | 1&2 | 0 | 0 | 0.5&1 | 0 | 0 |
| Mixture of Phenoxyethanol & Caprylyl Glycol | 0 | 0 | 0 | 0 | 0 | 0 | 1&2 | 0 | 0 | 0 | 0.5&1 |

The gloves were produced according to the method described in Example 1. Donning side of each set of glove was coated with prebiotic and probiotic coating composition described in Table 2.

Efficacy of the antimicrobial agent added into latex composition was evaluated using zone inhibition test. Test method is described below, 1. Trypticase soy agar (TSA) plate was prepared by dissolving TSA agar powder in deionised water.
2. Gram positive coccus strain was cultured and used in the zone inhibition test. A small amount of gram positive coccus cultured in agar plate was taken out from the plate before being dissolved in peptone water.
3. A 100 µL of peptone water containing bacteria was pipetted and spread evenly in the agar plate. Glove specimen with diameter of 1.6 cm was placed at the middle of agar plate surface. First latex layer was in contact with the agar plate.
4. The plates were then incubated at 36° C. in an incubator for 48 hours before the inhibition zone was measured. The inhibition zone is the zone in between the edge of glove specimen and the edge of clear zone that does not have bacteria growth.
5. Three points were measured and the average size of zone was recorded.
6. The size of zone inhibition indicates the efficacy of antimicrobial agent. Large inhibition zone indicates good bactericidal efficacy whereas small inhibition zone indicates weak bactericidal efficacy. The results are illustrated in Table 14.

TABLE 14

Size of zone inhibition for gloves produced with different antimicrobial agents.

| Set | Size of zone inhibition (mm) |
|---|---|
| Control | 2 |
| 1 | 5 |
| 2 | 8 |
| 3 | 3 |
| 4 | 4 |
| 5 | 3 |
| 6 | 3 |
| 7 | 2 |
| 8 | 1 |
| 9 | 2 |
| 10 | 3 |
| 11 | 4 |
| 12 | 2 |
| 13 | 2 |
| 14 | 5 |
| 15 | 5 |
| 16 | 5 |
| 17 | 4 |
| 18 | 7 |
| 19 | 6 |
| 20 | 5 |
| 21 | 5 |

Set 2 and Set 18 gloves showed good antimicrobial efficacy due to the larger zone inhibition compared with control.

Example 6: Antimicrobial Agent in Coagulant and First Latex Layer

Powder-free coagulant solution containing antimicrobial agent was prepared according to the coagulant composition described in Table 15 below.

TABLE 15

Powder-free coagulant composition containing antimicrobial agent.

| Ingredients | Percentage of composition (%) | | | | |
| --- | --- | --- | --- | --- | --- |
| | Set 1 | Set 2 | Set 3 | Set 4 | Control |
| Powder-free coagulant-metallic stearate (potassium and/or calcium stearate) | 1.5 | 1.5 | 1.5 | 1.5 | 1.5 |
| Wetting agent-alcohol ethoxylates (non-ionic surfactant) | 0.1 | 0.1 | 0.1 | 0.1 | 0.1 |
| Calcium nitrate | 13 | 13 | 13 | 13 | 13 |
| Phenoxyethanol | 0.1 | 0.2 | 0 | 0.1 | 0 |
| Mixture of phenoxyethanol, Caprylyl Glycol & Chlorphenesin | 0 | 0 | 0.1 | 0.1 | 0 |
| Water | 85.3 | 85.2 | 85.3 | 85.2 | 85.4 |

Gloves containing antimicrobial agents were prepared according to the latex composition described in Table 10, the dosage of zinc pyrithione was used at 1 phr instead of 1.5 phr. Dipping method described in Example 1 was used to produce the glove. Prebiotic and probiotic coating as described in Table 2 was used to coat on the donning side of gloves following post-leaching process. Control glove contained antimicrobial agent in the first latex layer only.

Efficacy of the antimicrobial agent added into powder-free coagulant solution and first latex layer composition was evaluated using zone inhibition test as in Table 16.

TABLE 16

Size of zone inhibition for glove containing antimicrobial agent in both the coagulant layer and first latex layer.

| Set | Size of inhibition zone (mm) |
| --- | --- |
| Control | 5 |
| 1 | 5 |
| 2 | 6 |
| 3 | 5 |
| 4 | 5 |

Addition of 0.2% phenoxyethanol in the coagulant layer has enhanced antimicrobial efficacy of the glove as the size of zone inhibition was slightly larger than control.

Example 7: Antimicrobial Agent in Coagulant Layer

Powder-free coagulant solution containing antimicrobial agent was prepared according to the coagulant composition described in Table 17 below.

TABLE 17

Powder-free coagulant composition containing antimicrobial agent.

| Ingredients | Percentage of composition (%) | | | | |
| --- | --- | --- | --- | --- | --- |
| | Set 1 | Set 2 | Set 3 | Set 4 | Control |
| Powder-free coagulant-metallic stearate (potassium and/or calcium stearate) | 1.5 | 1.5 | 1.5 | 1.5 | 1.5 |
| Wetting agent-alcohol ethoxylates (non-ionic surfactant) | 0.1 | 0.1 | 0.1 | 0.1 | 0.1 |
| Calcium nitrate | 13 | 13 | 13 | 13 | 13 |
| Phenoxyethanol | 0.2 | 0.1 | 0 | 0 | 0 |
| Mixture of phenoxyethanol, Caprylyl Glycol & Chlorphenesin | 0 | 0.1 | 0 | 0 | 0 |
| Zinc Pyrithione | 0 | 0 | 1 | 2 | 0 |
| Water | 85.2 | 85.2 | 84.4 | 83.4 | 85.4 |

Gloves were prepared according to Table 10 without zinc pyrithione in the first latex layer. Dipping method described in Example 1 was used to produce the glove. Prebiotic and probiotic coating composition described in Table 2 was used to coat on the donning side of gloves following post-leaching process. Control glove contains no antimicrobial agent.

Efficacy of the antimicrobial agent added into powder-free coagulant solution was evaluated using zone inhibition test as in Table 18.

TABLE 18

Size of inhibition zone for glove with antimicrobial agent in coagulant layer.

| Set | Size of inhibition zone (mm) |
| --- | --- |
| Control | 0 |
| 1 | 2 |
| 2 | 3 |
| 3 | 0 |
| 4 | 1 |

Mixtures of phenoxyethanol, Caprylyl Glycol & Chlorphenesin in Set 2 have shown good antimicrobial efficacy compared to zinc pyrithione.

Example 8: Antimicrobial Glove with and without Barrier Layer

Antimicrobial gloves with and without barrier layer were prepared according to the latex composition described in Table 19. Dipping method described in Example 1 was used to produce the glove. In order to determine the performance of barrier layer in reducing migration of antimicrobial agent from the surface layer, neither prebiotic nor probiotic was coated on the donning side of glove. No antimicrobial agent was added into powder-free coagulant composition. Control glove is absent of antimicrobial agent.

TABLE 19

Latex composition of antimicrobial glove with and without barrier layer.

| | Dosage (phr) | | | | | | |
|---|---|---|---|---|---|---|---|
| | First latex layer | Second latex layer | | | | | |
| Ingredients | | Set 1 | Set 2 | Set 3 | Set 4 | Set 5 | Set 6 |
| Carboxylated acrylonitrile latex | 100 | Without second latex layer (single dip) | 100 | 100 | 100 | 100 | 100 |
| Potassium hydroxide | 1.5 | | 1.5 | 1.5 | 1.5 | 1.5 | 1.5 |
| Stabiliser | 0.1 | | 0.1 | 0.1 | 0.1 | 0.1 | 0.1 |
| Sulfur | 0.15 | | 0.15 | 0.15 | 0.15 | 0.15 | 0.15 |
| Accelerator | 0.05 | | 0.05 | 0.05 | 0.05 | 0.05 | 0.05 |
| Zinc Oxide | 0.5 | | 0.3 | 0.3 | 0.3 | 0.3 | 0.3 |
| Antioxidant | 0.2 | | 0.2 | 0.2 | 0.2 | 0.2 | 0.2 |
| Titanium Dioxide | 2.0 | | 2.0 | 2.0 | 2.0 | 2.0 | 2.0 |
| Antifoam | 0.06 | | 0.06 | 0.06 | 0.06 | 0.06 | 0.06 |
| Zinc Pyrithione | 1.5 | | 0 | 0 | 0 | 0 | 0 |
| High lamellar Aluminium silicate | 0 | | 0 | 5 | 0 | 0 | 0 |
| High lamellar Talc | 0 | | 0 | 0 | 5 | 0 | 2.5 |
| High lamellar Leucophyllite | 0 | | 0 | 0 | 0 | 5 | 2.5 |

Performance of barrier layer in reducing migration of antimicrobial agent from the outer surface to the donning surface was evaluated using zone inhibition test. Test method was described in Example 5. Both outer surface (coagulant side) and inner surface (donning side) were evaluated and the outcome is illustrated in Table 20.

TABLE 20

Size of zone inhibition for gloves with and without barrier layer.

| | Size of inhibition zone (mm) | |
|---|---|---|
| Set | Coagulant side | Donning side |
| Control | 2 | 1 |
| 1 | 6 | 5 |
| 2 | 7 | 6 |
| 3 | 5 | 3 |
| 4 | 5 | 3 |
| 5 | 6 | 4 |
| 6 | 6 | 4 |

The barrier layer greatly reduces or prevents migration of antimicrobial agent from the outer surface to the donning side. Large zone inhibition was observed in both Set 1 and Set 2. Migration of antimicrobial agent was noticeable in Set 2, which has a second latex layer without lamellar filler. Inhibition zone reduced when barrier layer has been built with high lamellar fillers (aluminium silicate and talc) as the second latex layer.

Example 9: Antimicrobial Glove Made with Different Elastomers

Antimicrobial gloves made with different elastomers were prepared using latex composition described in Table 21. First latex layer was dipped with latex composition containing antimicrobial agent. Second latex layer was dipped with the same latex composition but without antimicrobial agent. Dipping method described in Example 1 was used to produce the glove. Prebiotic and probiotic coating composition described in Table 2 was used to coat on the donning side of gloves after post-leaching process. No antimicrobial agent was added into the coagulant composition.

TABLE 21

Latex composition of antimicrobial glove made with different elastomers.

| | Dosage (phr) | | | |
|---|---|---|---|---|
| Ingredients | Set 1 & 2 | Set 3 & 4 | Set 5 & 6 | Set 7 & 8 |
| Carboxylated acrylonitrile latex | 100 | 0 | 0 | 0 |
| Natural rubber latex | 0 | 100 | 0 | 0 |
| Polychloroprene latex | 0 | 0 | 100 | 0 |
| Polyurethane latex | 0 | 0 | 0 | 100 |
| Potassium hydroxide | 1.5 | 0.2 | 0.3 | 0.5 |
| Stabiliser | 0.1 | 0.1 | 0.1 | 0.1 |
| Sulfur | 0.15 | 1.2 | 1 | 0 |
| Accelerator | 0.05 | 0.4 | 1 | 0 |
| Zinc Oxide | 0.5 | 0.4 | 2 | 0 |
| Antioxidant | 0.2 | 0.6 | 0.2 | 0.2 |
| Titanium Dioxide | 2.0 | 0.5 | 2.0 | 2.0 |
| Polycarbodiimide crosslinker | 0 | 0 | 0 | 0.1 |
| Calcium carbonate (anti-tack for natural rubber) | 0 | 10 | 0 | 0 |
| Antifoam | 0.06 | 0.06 | 0.06 | 0.06 |
| Zinc Pyrithione | 1 & 2 | 1 & 2 | 1 & 2 | 1 & 2 |

Efficacy of the antimicrobial gloves made with different elastomers was evaluated according to method described in Example 5. For antimicrobial efficacy, coagulant side was used as the contact surface with TSA agar plate. Performance of prebiotic and probiotic coating was evaluated using method described in Example 4. For the performance of prebiotic and probiotic coating, donning surface was used as the contact surface with MRS agar plate.

TABLE 22

Size of zone inhibition for gloves made with different elastomers.

| | Size of inhibition zone (mm) | |
|---|---|---|
| Set | Coagulant side (antimicrobial efficacy) | Donning side (prebiotic & probiotic coating performance) |
| 1 | 6 | 2 |
| 2 | 7 | 2 |
| 3 | 3 | 2 |
| 4 | 4 | 3 |
| 5 | 6 | 2 |
| 6 | 5 | 3 |
| 7 | 5 | 3 |
| 8 | 6 | 3 |

The antimicrobial agent can be added into different elastomer to form an elastomeric article having antimicrobial properties. Smaller zone inhibition was observed in natural rubber samples (Set 3 & 4), indicating that more antimicrobial agent is needed for natural rubber latex due to its weaker antimicrobial efficacy compared with other type of elastomers.

Example 10: Antimicrobial Efficacy Before and After Accelerated Aging

The gloves produced in Example 1 were aged at 100° C. for 22 hours. Antimicrobial efficacy of the aged gloves was tested using zone inhibition method as described in Example 5.

TABLE 23

Size of zone inhibition for both the unaged and aged antimicrobial gloves.

| Set | Zinc pyrithione dosage (phr) | Size of inhibition zone (mm) Unaged | Aged at 100° C., 22 hours |
|---|---|---|---|
| Control | 0 | 0 | 0 |
| 1 | 1.0 | 6 | 5 |
| 2 | 2.0 | 7 | 5 |
| 3 | 3.0 | 7 | 4 |
| 4 | 4.0 | 8 | 6 |

Antimicrobial efficacy of the antimicrobial glove was slightly deteriorated after accelerated aging. This could be due to thermal instability of zinc pyrithione. Nevertheless, the remaining antimicrobial efficacy was still significant, and much higher than the control.

Example 11: Prebiotic and Probiotic Efficacy after Aging

The selected gloves coated with prebiotic/probiotic from Example 4 were further aged at 70° C. for 7 days. The skin protectant efficacy was performed using zone inhibition test method as described in Example 4.

TABLE 23

| Glove coating at inner layer | Size of zone inhibition (mm) after aging |
|---|---|
| Mixture of xylitol & lactitol (Brand: Ecodermine ™) at 4% | 2 |
| *Lactobacillus* ferment lysate (4%) | 3 |
| Control (without coating) | 5 |

*Lactobacillus casei* growth was inhibited within a 5 mm zone from the control glove, but growth was less inhibited (i.e. it was improved compared to the control) as demonstrated by the smaller sized zone of inhibition.

Example 12: Physical Properties of Antimicrobial Glove

The physical properties of some of the present antimicrobial gloves were compared following accelerated aging. The accelerated aging was conducted at 100° C. for 22 hours.

Glove A denotes the control glove.

Glove B denotes the antimicrobial glove having Zinc Pyrithione (1.5%) in the first latex layer and a coating mixture of Ecodermine™ (2%) and *Lactobacillus* ferment lysate (2%) at the inner layer of glove.

Glove C denotes the Glove B containing a barrier layer in the second latex layer, which is made up of lamellar aluminium silicate according to Example 8.

TABLE 24

Physical property comparisons before and after aging.

| | Unaged | | | Aged | | |
|---|---|---|---|---|---|---|
| | A | B | C | A | B | C |
| Tensile strength (MPa) | 27.1 | 26.4 | 23.5 | 29.3 | 30.3 | 25.2 |
| Elongation (%) | 820 | 830 | 750 | 790 | 750 | 650 |
| Modulus at 500% elongation (MPa) | 4.6 | 4.3 | 5.2 | 4.5 | 4.8 | 6.3 |

These results indicate that, despite the presence of the antimicrobial and the skin-protective agent, and also the lamellar filler (in the case of Glove C), the glove qualities were not markedly inferior to the control containing neither the antimicrobial nor the skin-protective agent (nor lamellar filler).

Example 13

Antimicrobial efficacy of glove containing Zinc Pyrithione (1.5%) in the first latex layer (external glove surface) and a 4% *Lactobacillus* ferment lysate composition on the internal glove surface was used against both beneficial (*Lactobacillus casei*) and harmful (*Staphylococcus aureus*) microorganism cultures. *Lactobacillus casei* and *Staphylococcus aureus* was cultured in MRS (methods described in Example 4) and TSA (methods described in Example 5) agar plate, respectively, for glove samples with the external surface facing downwardly, and the internal surface facing downwardly. The zone inhibition was measured after 48 hours incubation at 36° C. A glove of the same description but without antimicrobial agent was used as control (the external face of that glove was placed downwardly on the plate.

TABLE 25

Antimicrobial efficacy of Zinc pyrithione surface, and *Lactobacillus* ferment lysate surface, against beneficial and harmful bacteria.

| | Size of zone inhibition (mm) in *Lactobacillus casei* culture | Size of zone inhibition (mm) in *Staphylococcus aureus* culture |
|---|---|---|
| Glove face containing 1.5% Zinc Pyrithione | 10 | 9 |
| Glove face containing a 4% *Lactobacillus* ferment lysate | 2 | 4 |
| Control glove | 3 | 2 |

The results demonstrate the efficacy of the external antimicrobial surface of the glove against harmful bacterial (and beneficial bacteria). The internal surface of the glove shows better growth support for beneficial bacteria compared to harmful bacteria (only minimal adverse impact on the growth of beneficial bacteria). The internal surface of the glove does not demonstrate a significant antimicrobial affect against both beneficial and harmful bacterial, as indicated by the fact that the zone of inhibition of each is less than 4 mm. If an effective amount of antibacterial agent was present on the internal surface, the zone of inhibition of both bacterial types would be greater than 4 mm.

Items:

1A. An elastomeric article comprising:
an elastomeric film comprising one or more film layers, and including an external surface and an internal surface, an antimicrobial agent on the external surface of the elastomeric film, and a skin-protective agent selected from a probiotic, a prebiotic, or a combination thereof on the internal surface of the elastomeric film.

1B. An elastomeric article comprising:

an elastomeric film comprising one or more film layers, and including an external surface and an internal surface, an antimicrobial agent that is effective against both beneficial and harmful microorganisms on the external surface of the elastomeric film, and a skin-protective agent selected from a probiotic, a prebiotic, or a combination thereof on the internal surface of the elastomeric film, wherein the inner surface of the film is free of an antimicrobially-effective amount of an antimicrobial agent that is effective against both beneficial and harmful microorganisms.

1C. An elastomeric article comprising:

an elastomeric film comprising one or more film layers, and including an external surface and an internal surface, an antimicrobial agent on the external surface of the elastomeric film, and a skin-protective agent selected from a probiotic, a prebiotic, or a combination thereof on the internal surface of the elastomeric film, wherein the film has:

a modulus at 500% stretch of less than 15 MPa;

a modulus at 300% stretch of less than 10 MPa;

a tensile strength of at least 8 MPa; and/or an elongation to break of at least 200%.

1D. An elastomeric article comprising:

an elastomeric film comprising one or more film layers, and including an external surface and an internal surface, an antimicrobial agent on the external surface of the elastomeric film, and a skin-protective agent selected from a probiotic, an isolated prebiotic, or a combination thereof on the internal surface of the elastomeric film.

2. The elastomeric article of item 1, further comprising a barrier layer that provides separation between the antimicrobial agent and the skin-protective agent.

3. The elastomeric article of item 2, wherein the barrier layer is a barrier film layer or a barrier coating layer.

4. The elastomeric article of any one of items 1 to 3, wherein the elastomeric film is a single layer film.

5. The elastomeric article of any one of items 1 to 3, wherein the elastomeric film is a multilayer film comprising a first film layer that defines the external surface of the article and a second film layer that defines the internal surface of the article.

6. The elastomeric article of item 5, wherein the antimicrobial agent is present within the first film layer.

7. The elastomeric article of item 6, wherein the antimicrobial agent is present in the first film layer through incorporation into a coagulant used in the production of the elastomeric article, or through incorporation into an elastomeric film-forming composition used to produce the first film layer.

8. The elastomeric article of item 7, wherein the amount of antimicrobial agent in the first film layer is 0.01 to 20 phr.

9. The elastomeric article of any one of items 1 to 7, wherein the article comprises a coating layer on the external surface of the article, and the coating layer on the external surface comprises the antimicrobial agent.

10. The elastomeric article of any one of items 1 to 9, wherein the skin-protective agent is present in a coating on the internal surface of the elastomeric film.

11. The elastomeric article of any one of items 1 to 10, wherein the article comprises a coating layer on the internal surface of the article, and the coating layer on the internal surface comprises the skin-protective agent.

12. The elastomeric article of item 11, wherein the coating layer constitutes about 0.001% to about 30% by weight of the total weight of the article.

13. The elastomeric article of item 11 or item 12, wherein the total amount of the skin-protective agent in the coating layer is at least 5% by weight of the coating layer.

14. The elastomeric article of any one of items 1 to 13, wherein the antimicrobial agent is selected from the group consisting of pyrithiones, phenolic compounds, heterocyclic compounds, quaternary ammonium salts, biguanide compounds, parabens, antibiotics, antivirals, antifungals, antimicrobial peptides and combinations of one or more thereof.

15. The elastomeric article of item 14, wherein the antimicrobial agent is selected from the group consisting of pyrithiones, phenolic compounds, and combinations thereof.

16. The elastomeric article of any one of items 1 to 15 wherein the skin-protective agent comprises a probiotic is selected from the group consisting of *Lactobacillus, Lactococcus, Bifidobacterium*, and combinations thereof.

17. The elastomeric article of any one of items 1 to 16, wherein the skin-protective agent comprises a prebiotic selected from the group consisting of saccharides, phytosphingosine and derivatives or salts thereof, lactic acid, glycomacropeptide, amino acids, peptides and combinations thereof.

18. The elastomeric article of item 17, wherein the prebiotic comprises a saccharide selected from the group consisting of alpha-glucan, beta-glucan, fructooligosaccharides, inulin, and combinations thereof.

19. The elastomeric article of any one of items 1 to 18, wherein the elastomeric film comprises an elastomer selected from the group consisting of natural rubber, nitrile rubber, silicone rubber, polyvinyl chloride, polyethylene, polypropylene, polyurethane, polyisoprene, polychloroprene, polystyrene, acrylic polymers, polybutadienes, fluoroelastomers, copolymers or blends of these polymers or their monomers, and derivatives or blends thereof.

20. The elastomeric article of any one of items 1 to 19, wherein the elastomeric film comprises an elastomer selected from the group consisting of natural rubber, nitrile rubber, polyisoprene, polychloroprene, polyurethane, copolymers or blends of these polymers or their monomers, and derivatives or blends thereof.

21. The elastomeric article of any one of items 1 to 20, in the form of a glove, finger cot or footwear.

22. The elastomeric article of any one of items 1 to 21, wherein the article has an average thickness of between 0.01 and 3.0 mm.

23. The elastomeric article of any one of items 1 to 22, with:

a modulus at 500% stretch of less than 15 MPa, a modulus at 300% stretch of less than 10 MPa, a tensile strength of at least 8 MPa; and/or an elongation to break of at least 200%.

24A. A method for the manufacture of an elastomeric article, the method comprising:
  providing an elastomeric film comprising one or more film layers, the elastomeric film including first and second opposing surfaces;
  introducing an antimicrobial agent onto or into the first opposing surface; and
  introducing a skin-protective agent selected from a probiotic, a prebiotic, or a combination thereof onto or into the second opposing surface.

24B. A method for the manufacture of an elastomeric article, the method comprising:
  providing an elastomeric film comprising one or more film layers, the elastomeric film including first and second opposing surfaces;
  introducing an antimicrobial agent that is effective against both beneficial and harmful microorganisms onto or into the first opposing surface in a manner so as to avoid the antimicrobial agent from being introduced onto or into the second opposing surface; and
  introducing a skin-protective agent selected from a probiotic, a prebiotic, or a combination thereof onto or into the second opposing surface.

24C. A method for the manufacture of an elastomeric article, the method comprising:
  providing an elastomeric film comprising one or more film layers, the elastomeric film including first and second opposing surfaces;
  introducing an antimicrobial agent onto or into the first opposing surface; and introducing a skin-protective agent selected from a probiotic, a prebiotic, or a combination thereof onto or into the second opposing surface,
  the method further comprising preparing the film with the antimicrobial agent and skin-protective agent whist maintaining film properties of:
  a modulus at 500% stretch of less than 15 MPa;
  a modulus at 300% stretch of less than 10 MPa;
  a tensile strength of at least 8 MPa; and/or
  an elongation to break of at least 200%.

24D. A method for the manufacture of an elastomeric article, the method comprising:
  providing an elastomeric film comprising one or more film layers, the elastomeric film including first and second opposing surfaces;
  introducing an antimicrobial agent onto or into the first opposing surface; and
  introducing a skin-protective agent selected from a probiotic, an isolated prebiotic, or a combination thereof onto or into the second opposing surface.

25. The method of item 24, comprising incorporating a barrier layer that provides separation between the antimicrobial agent and the skin-protective agent.

26. The method of item 25, comprising incorporating the barrier layer into the elastomeric article as a barrier film layer or a barrier coating layer.

27. The method of item 26, the method comprising producing a first film layer from a first elastomeric film-forming composition which comprises the antimicrobial agent so as to result in the introduction of the antimicrobial agent into the first opposing surface of the article, and producing the barrier film layer as a separate layer of the elastomeric film.

28. The method of item 27, comprising dipping a mould into the first elastomeric film-forming composition to produce the first film layer, and dipping the mould into a second elastomeric film-forming composition to form the barrier film layer.

29. The method of item 27 or item 28, comprising incorporating the antimicrobial agent into the first elastomeric film-forming composition in an amount of from 0.01 to 20 phr.

30. The method of item 26, the method comprising:
  dipping a mould into a coagulant composition comprising the antimicrobial agent and dipping the coagulant-dipped mould into a first elastomeric film-forming composition to produce a first film layer of the elastomeric film, the dipping steps resulting in the incorporation of the antimicrobial agent into the first film layer; and
  dipping the mould with the first film layer into a second elastomeric film-forming composition to form the barrier film layer.

31. The method of item 30, comprising incorporating the antimicrobial agent into the coagulant composition in an amount of from about 0.01% to about 50% by weight of the coagulant composition.

32. The method of any one of items 24 to 31, comprising coating a coating composition comprising the antimicrobial agent onto the first opposing surface of the elastomeric film.

33. The method of item 32, comprising spray coating or tumble coating the coating composition onto the first opposing surface of the elastomeric film.

34. The method of any one of items 24 to 33, comprising coating a coating composition comprising the skin-protective agent onto the second opposing surface of the elastomeric film.

35. The method of item 34, comprising coating a coating composition comprising a skin-protective agent in an amount of between about 0.01% and about 50% by weight of the coating composition onto the second opposing surface of the elastomeric film.

36. The method of item 34, comprising coating a coating composition comprising a skin-protective agent in an amount of between about 0.01% and about 30% by weight of the coating composition onto the second opposing surface of the elastomeric film.

37. The method of item 35 or item 36, comprising dip coating, spray coating or tumble coating the coating composition onto the second opposing surface of the elastomeric film.

38. The method of any one of items 34 to 37, wherein the coating composition coated onto the second opposing surface of the elastomeric film comprises:
  0.01-20% by weight of the skin-protective agent;
  optionally one or more of a dispersing agent, an emulsifier, a solubiliser, a rheology modifier, a wetting agent, an emollient, a skin conditioning agent, a humectant, a biocide, a preservative, silicone, fragrance and a pH adjustor; and
  water.

39. The method of any one of items 34 to 38, comprising applying the coating composition comprising the skin-protective agent onto the elastomeric film by dipping or spray coating in an online process prior to curing of the elastomeric film.

40. The method of any one of items 28 to 31, comprising dipping the mould with the first elastomeric film layer comprising the antimicrobial agent and the barrier layer into a third elastomeric film-forming composition comprising the skin-protective agent, to produce a third film layer comprising the skin-protective agent.

41. The method of item 40, wherein the step of dipping the mould into the third elastomeric film-forming composition comprises dipping into a third elastomeric film-forming composition comprising 0.01-50 phr of skin-protective agent.

42. The method of item 24, comprising applying a coating composition comprising the antimicrobial agent onto the first surface of the elastomeric film, and applying a coating composition comprising the skin-protective agent onto the second opposing surface of the elastomeric film.

43. An elastomeric article comprising:
an elastomeric film comprising one or more film layers, and including an external surface and an internal surface,
an antimicrobial agent on the external surface of the elastomeric film,
a skin-protective agent selected from a probiotic, a prebiotic, or a combination thereof on the internal surface of the elastomeric film, and
a barrier film layer that provides separation between the antimicrobial agent and the skin-protective agent.

44. A method for the manufacture of an elastomeric article, the method comprising:
providing an elastomeric film comprising one or more film layers, the elastomeric film including first and second opposing surfaces;
introducing an antimicrobial agent onto or into the first opposing surface;
introducing a skin-protective agent selected from a probiotic, a prebiotic, or a combination thereof onto or into the second opposing surface; and
providing a barrier film layer in the elastomeric film that provides separation between the antimicrobial agent and the skin-protective agent.

45. The elastomeric article produced by any one of items 24 to 42 and 44.

46. An elastomeric article comprising:
an elastomeric film comprising one or more film layers, and including an external surface and an internal surface;
an antimicrobial agent that is effective against both beneficial and harmful microorganisms on the external surface of the elastomeric film; and
a barrier film layer between the antimicrobial agent on the external surface of the elastomeric film and the internal surface, to prevent contact between the antimicrobial agent and skin that comes into contact with the internal surface of the article, wherein the internal surface of the film is free of an antimicrobially-effective amount of an antimicrobial agent that is effective against both beneficial and harmful microorganisms.

47. The elastomeric article of item 46, wherein the film layers include a first film layer and said barrier film layer, and wherein the antimicrobial agent is present in said first film layer through incorporation into a coagulant used in the production of the elastomeric article, or through incorporation into an elastomeric film-forming composition used to produce the first film layer.

48. The elastomeric article of item 46 or item 47, with:
a modulus at 500% stretch of less than 15 MPa,
a modulus at 300% stretch of less than 10 MPa,
a tensile strength of at least 8 MPa; and/or
an elongation to break of at least 200%.

49. The elastomeric article of any one of items 46 to 48, wherein the antimicrobial agent is selected from the group consisting of pyrithiones, phenolic compounds, heterocyclic compounds, quaternary ammonium salts, biguanide compounds, parabens, antibiotics, antivirals, antifungals, antimicrobial peptides and combinations of one or more thereof.

50. The elastomeric article of any one of items 46 to 49, wherein the number of said film layers is two, including a first film layer comprising said antimicrobial agent and said barrier film layer, and wherein the first film layer is on one side of the barrier film layer, and a polymer coating and/or a donning coating is on the opposite side of the barrier film layer.

The invention claimed is:

1. An elastomeric article comprising:
an elastomeric film comprising one or more film layers, and including an external surface and an internal surface,
an antimicrobial agent that is effective against both beneficial and harmful microorganisms on the external surface of the elastomeric film,
a dry, dehydrated coating layer on the internal surface of the elastomeric film comprising a skin-protective agent selected from a probiotic, a prebiotic, or a combination thereof, and
a barrier film layer that provides separation between the antimicrobial agent and the skin-protective agent and substantially prevents migration of the antimicrobial agent to the internal surface of the elastomeric film, wherein the internal surface of the elastomeric film is free of an antimicrobially-effective amount of an antimicrobial agent that is effective against both beneficial and harmful microorganisms.

2. The elastomeric article of claim 1, wherein the elastomeric film is a multilayer film comprising a first film layer that defines the external surface of the article and a second film layer that defines the internal surface of the article.

3. The elastomeric article of claim 2, wherein the antimicrobial agent is present within the first film layer.

4. The elastomeric article of claim 3, wherein the antimicrobial agent is present in the first film layer through incorporation into a coagulant used in the production of the elastomeric article, or through incorporation into an elastomeric film-forming composition used to produce the first film layer.

5. The elastomeric article of claim 4, wherein the amount of antimicrobial agent in the first film layer is 0.01 to 20 phr.

6. The elastomeric article of claim 1, wherein the article comprises a coating layer on the external surface of the article, and the coating layer on the external surface comprises the antimicrobial agent.

7. The elastomeric article of claim 1, wherein the total amount of the skin-protective agent in the coating layer is at least 5% by weight of the coating layer.

8. The elastomeric article of claim 1, wherein the antimicrobial agent is selected from the group consisting of pyrithiones, phenolic compounds, heterocyclic compounds, quaternary ammonium salts, biguanide compounds, parabens, antibiotics, antivirals, antifungals, antimicrobial peptides and combinations of one or more thereof.

9. The elastomeric article of claim 1, wherein the skin-protective agent comprises a probiotic is selected from the group consisting of *Lactobacillus, Lactococcus, Bifidobacterium*, and combinations thereof.

10. The elastomeric article of claim 1, wherein the skin-protective agent comprises a prebiotic selected from the group consisting of saccharides, phytosphingosine and derivatives or salts thereof, lactic acid, glycomacropeptide, amino acids, peptides and combinations or salts thereof.

11. The elastomeric article of claim 1, wherein the elastomeric film comprises an elastomer selected from the group consisting of natural rubber, nitrile rubber, silicone rubber, polyvinyl chloride, polyethylene, polypropylene, polyurethane, polyisoprene, polychloroprene, polystyrene, acrylic polymers, polybutadienes, fluoroelastomers, copolymers or blends of these polymers or their monomers, and derivatives or blends thereof.

12. The elastomeric article of claim 1, in the form of a glove, finger cot or footwear.

13. The elastomeric article of claim 1, wherein the article has an average thickness of between 0.01 and 3.0 mm.

14. The elastomeric article of claim 13, with:
a modulus at 500% stretch of less than 15 MPa,
a modulus at 300% stretch of less than 10 MPa,
a tensile strength of at least 8 MPa; and/or
an elongation to break of at least 200%.

15. A method for the manufacture of an elastomeric article, the method comprising:
providing an elastomeric film comprising one or more film layers, the elastomeric film including first and second opposing surfaces;
introducing an antimicrobial agent that is effective against both beneficial and harmful microorganisms onto or into the first opposing surface in a manner so as to avoid the antimicrobial agent from being introduced onto or into the second opposing surface;
applying a coating composition comprising a skin-protective agent selected from a probiotic, a prebiotic, or a combination thereof onto the second opposing surface and drying the coating composition to form a dry, dehydrated coating layer, and
providing a barrier film layer in the elastomeric film that provides separation between the antimicrobial agent and the skin-protective agent and substantially prevents migration of the antimicrobial agent to the second opposing surface of the elastomeric film,
wherein the second opposing surface of the elastomeric article produced by the method is free of an antimicrobially-effective amount of antimicrobial agent.

16. An elastomeric article comprising:
an elastomeric film comprising one or more film layers, and including an external surface and an internal surface;
an antimicrobial agent that is effective against both beneficial and harmful microorganisms on the external surface of the elastomeric film; and
a barrier film layer between the antimicrobial agent on the external surface of the elastomeric film and the internal surface that substantially prevents migration of the antimicrobial agent to the internal surface of the elastomeric film, to prevent contact between the antimicrobial agent and skin that comes into contact with the internal surface of the article,
wherein the internal surface of the elastomeric film is free of an antimicrobially-effective amount of an antimicrobial agent that is effective against both beneficial and harmful microorganisms.

17. The elastomeric article of claim 1, wherein the skin-protective agent comprises one or more of:
a probiotic selected from the group consisting of *Lactobacillus, Lactococcus, Bifidobacterium*, and combinations thereof; and
a prebiotic selected from the group consisting of saccharides, phytosphingosine and derivatives or salts thereof, lactic acid, glycomacropeptide, amino acids, peptides and combinations or salts thereof.

18. The elastomeric article of claim 4, wherein the amount of antimicrobial agent in the first film layer is 0.1 to 10 phr.

19. The elastomeric article of claim 1, wherein the probiotic is in the form of a ferment lysate or extract.

20. The method of claim 15, wherein the probiotic is in the form of a ferment lysate or extract.

21. The elastomeric article of claim 1, wherein the skin-protective agent comprises both the probiotic and the prebiotic.

22. The method of claim 15, wherein the skin-protective agent comprises both the probiotic and the prebiotic.

* * * * *